United States Patent [19]

Huser et al.

[11] Patent Number: 4,977,160
[45] Date of Patent: Dec. 11, 1990

[54] BCD TRICYCLIC ERGOLINE PART-STRUCTURE ANALOGUES

[75] Inventors: Diane L. Huser; John M. Schaus, both of Indianapolis, Ind.

[73] Assignee: Eli Lilly and Company, Indianapolis, Ind.

[21] Appl. No.: 311,904

[22] Filed: Feb. 16, 1989

Related U.S. Application Data

[62] Division of Ser. No. 874,741, Jun. 16, 1986, Pat. No. 4,826,986.

[51] Int. Cl.$^5$ ............... C07D 487/04; A61K 31/435; A61K 31/47
[52] U.S. Cl. .................................... 514/293; 546/82; 546/83; 546/84; 546/153; 546/156; 546/159; 546/162; 546/164; 546/169; 546/170; 546/178; 546/171
[58] Field of Search ................... 546/82; 514/293

[56] References Cited

U.S. PATENT DOCUMENTS

| | | | |
|---|---|---|---|
| 4,198,415 | 4/1980 | Kornfeld et al. | 546/82 |
| 4,230,861 | 10/1980 | Kornfeld et al. | 546/82 |
| 4,235,909 | 11/1980 | Bach et al. | 546/84 |
| 4,273,932 | 6/1981 | Matsubara et al. | 546/156 |
| 4,468,401 | 8/1984 | Hahn | 546/82 |
| 4,471,121 | 9/1984 | Schaus et al. | 546/164 |
| 4,501,890 | 2/1985 | Nichols et al. | 514/267 |
| 4,525,584 | 6/1985 | Gallick-Whitaker | 546/82 |
| 4,537,893 | 8/1985 | Titus et al. | 514/293 |
| 4,647,667 | 3/1987 | Schaus | 546/164 |
| 4,659,832 | 4/1987 | Schaus et al. | 546/83 |
| 4,778,894 | 10/1988 | Schaus et al. | 546/164 |
| 4,826,986 | 5/1989 | Huser et al. | 546/153 |

OTHER PUBLICATIONS

Bach et al., *J. Med. Chem.*, 23, 481 (1980).
Nordman et al., *J. Med. Chem.*, 28(3), 367 (1985).

*Primary Examiner*—Mukund J. Shah
*Assistant Examiner*—E. Bernhardt
*Attorney, Agent, or Firm*—Douglas J. Taylor; Leroy Whitaker

[57] ABSTRACT

7- or 8-Substituted, partially hydrogenated pyrazolo[3,4-g]quinoline, thiazolo[4,5-g]quinoline, oxazolo[4,5-g]quinoline, and pyrrolo[3,4-g]quinoline derivatives, and 8- or 9-substituted, partially hydrogenated pyrido[2,3-g]quinazoline derivatives are D-2 dopamine agonists. 6-Oxo-1-substituted-octahydroquinolines and 6-oxo-1-substituted-decahydroquinolines which are additionally substituted in the 3- or 4-position are intermediates useful in preparation of the dopamine agonists. Acetals of 4,6-dioxo-1-substituted-decahydroquinoline 3-carboxylic acid esters enable synthesis of the foregoing compounds.

15 Claims, No Drawings

BCD TRICYCLIC ERGOLINE PART-STRUCTURE ANALOGUES

This application is a division, of application Ser. No. 06/874,741, filed June 16, 1986 now U.S. Pat. No. 4,826,986, issued May 2, 1989.

This invention relates to ergoline analogues, and more particularly to BCD tricyclic ergoline part-structure analogues, to intermediates used to prepare such analogues, and to use of such analogues as dopamine agonists.

BACKGROUND OF THE INVENTION

The ergoline ring is a tetracycle having the following structure

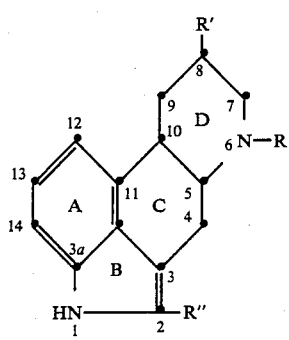

Certain substituted ergolines are known to be D-2 dopamine agonists having the ability to inhibit the secretion of prolactin and to affect favorably the symptoms of Parkinson's Syndrome. For example, in the foregoing structure when R is n-propyl, R' is methylthiomethyl, and R" is H, the substituted ergoline has been given the generic name pergolide. It is disclosed in U.S. Pat. No. 4,166,182. Pergolide is on clinical trial for the treatment of Parkinsonism and for certain conditions in which there is an excess of circulating prolactin, i.e., galactorrhea and inappropriate lactation. Another such ergoline drug is α-bromoergocryptine, named generically as bromocriptine. It is disclosed in U.S. Pat. Nos. 3,752,814 and 3,752,888. For bromocriptine R" is Br, R is methyl and R' is the ergocryptine side chain. While both ergolines are D-2 dopamine agonists, bromocriptine, and to a lesser extent pergolide, also have some alpha blocking activity.

BCD tricyclic ergoline part-structure compounds having the following formula

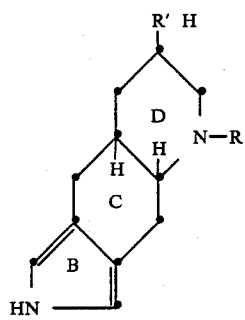

wherein R is lower alkyl, have been synthesized, and are disclosed in Bach et al, *J. Med. Chem.*, 23, 481 (1980) and U.S. Pat. No. 4,235,909. These products were prepared as racemates composed of the enantiomer illustrated above together with the mirror image thereof. In both enantiomers the R' substituent is equatorial. These compounds show activity in prolactin inhibition and rat-turning behavior tests, indicating that D-2 dopamine agonist activity is present. Related compounds in which the C-1 carbon is replaced by nitrogen to form a pyrazole ring are also disclosed by Bach et al. in *J. Med. Chem.*, 23, 481 (1980) and in U.S. Pat. No. 4,198,415. These pyrazoloquinolines are also D-2 dopamine agonists, and they too were prepared only as the racemate wherein the R' substituent of each enantiomer is equatorial.

SUMMARY OF THE INVENTION

This invention provides BCD tricyclic ergoline part-structure analogues of the formula (1)

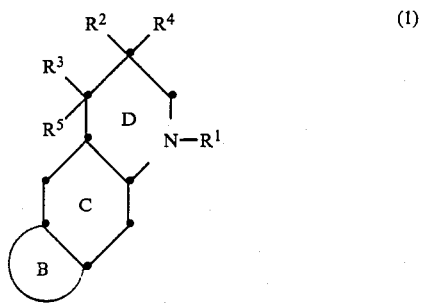 (1)

wherein:
the C and D rings are trans fused;
$R^1$ is ($C_1$-$C_3$) alkyl, allyl, or cyclopropylmethyl;
$R^2$ is hydrogen, $CH_2OH$, $CH_2OCH_3$, $CH_2SCH_3$, $CH_2SOCH_3$, $CH_2SO_2CH_3$, $CO_2R^6$, or $CONR^7R^8$, where $R^6$ is hydrogen, ($C_1$-$C_4$)alkyl or benzyl, and $R^7$ and $R^8$ are independently selected from hydrogen, ($C_1$-$C_4$)alkyl, phenyl, benzyl, and phenethyl;
$R^3$ is hydrogen, OH, $NH_2$, $NHCOR^9$ or $NHSO_2NR^9R^{10}$, where $R^9$ and $R^{10}$ are independently selected from hydrogen, ($C_1$-$C_4$)alkyl, and phenyl, or $R^3$ and $R^5$ combine to form =O or =NOH;
$R^4$ and $R^5$ are both hydrogen, or combine to form a carbon-carbon bond, except that $R^4$ is hydrogen when $R^5$ combines with $R^3$ to form =O or =NOH;
provided that one of $R^2$ and $R^3$ is hydrogen and the other is not hydrogen, and further provided that $R^2$ is hydrogen unless $R^4$ and $R^5$ combine to form a carbon-carbon bond; and

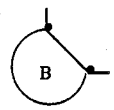

represents

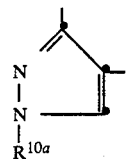 (a)

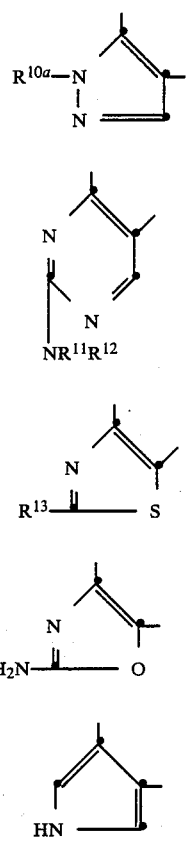

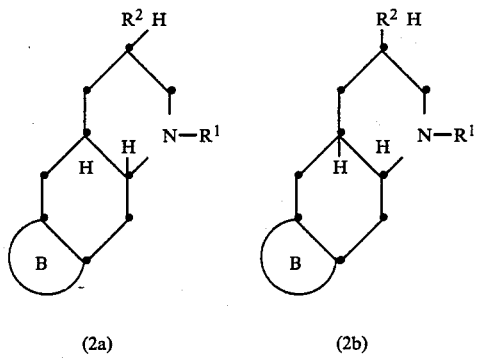
(2a)　　　(2b)

where
R¹ is (C₁–C₃) alkyl, allyl, or cyclopropylmethyl;
R² is $CH_2OH$, $CH_2OCH_3$, $CH_2SCH_3$, $CH_2SOCH_3$, $CH_2SO_2CH_3$, $CO_2R^6$, or $CONR^7R^8$, where $R^6$ is hydrogen, (C₁–C₄)alkyl or benzyl, and $R^7$ and $R^8$ are independently selected from hydrogen, (C₁–C₄)alkyl, phenyl, benzyl, and phenethyl; and
B is as defined for formula (1), and pharmaceutically acceptable acid addition salts thereof. Compounds of formula (2a) and (2b) are enantiomers. When "compounds of formula (2)" are referred to hereinafter, the racemate is intended.

The invention also provides BC tricyclic ergoline part-structure analogues having the following structures (3a) and (3b)

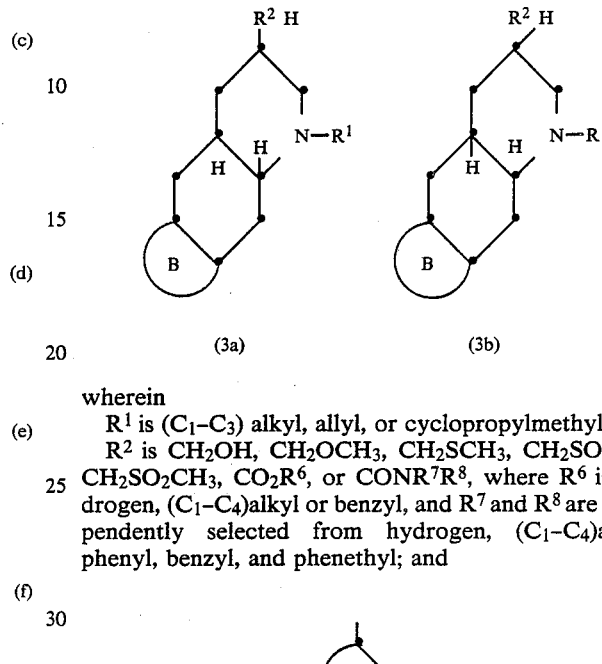
(3a)　　　(3b)

wherein
R¹ is (C₁–C₃) alkyl, allyl, or cyclopropylmethyl; and
R² is $CH_2OH$, $CH_2OCH_3$, $CH_2SCH_3$, $CH_2SOCH_3$, $CH_2SO_2CH_3$, $CO_2R^6$, or $CONR^7R^8$, where $R^6$ is hydrogen, (C₁–C₄)alkyl or benzyl, and $R^7$ and $R^8$ are independently selected from hydrogen, (C₁–C₄)alkyl, phenyl, benzyl, and phenethyl; and

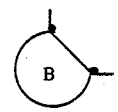

represents

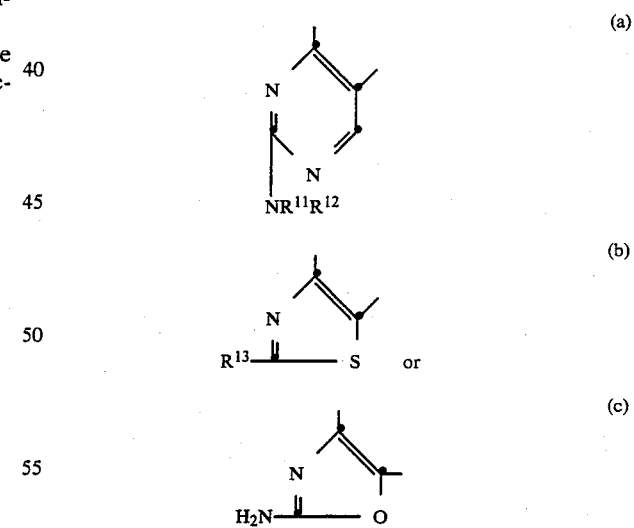

wherein $R^{11}$, $R^{12}$, and $R^{13}$ are as defined in formula (1), and pharmaceutically acceptable acid addition salts thereof. Compounds of formulas (3a) and (3b) are enantiomers, and reference to "compounds of formula (3)" means the racemate.

The pharmaceutically-acceptable acid addition salts of compounds of formulas (1), (2) and (3) include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

The synthetic procedures discussed herein produce compounds of formulas (1), (2), and (3) as racemates.

In the case of compounds of formula (1) wherein $R^2$ is other than hydrogen and $R^4$ and $R^5$ combine to form a carbon-carbon bond, the racemates produced are composed of enantiomers having the structures

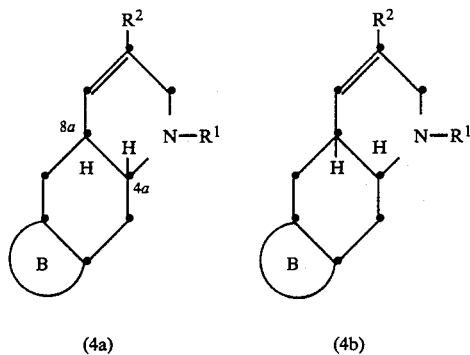

(4a)　　　　(4b)

in naming these products herein, the racemate is not explicitly indicated, but it is to be understood that such products are racemates. Accordingly, products of this type are named as:

(a) trans-4,4a,5,6,7,8,8a,9-hexahydro-2-H-pyrazolo[3,4-g]quinolines, (b) trans-4,4a,5,6,7,8,8a,9-hexahydro-1-H-pyrazolo[3,4-g]quinolines, (c) trans-5,5a,6,7,8,9,9a,10-hexahydropyrido-[2,3-g]quinazolines, (d) trans-4,4a,5,6,7,8,8a,9-hexahydrothiazolo-[4,5-g]quinazolines, (e) trans-4,4a,5,6,7,8,8a,9-hexahydrooxazolo-[4,5-g]quinolines, and (f) trans-4,4a,5,6,7,8,8a,9-hexahydropyrrolo-[3,4-g]quinolines.

The 4,4a,5,6,8a,9-hexahydro-2H-pyrazolo[3,4-g]quinolines (a) and the corresponding 4,4a,5,6,8a,9-hexahydro-1H-pyrazolo[3,4-g]quinolines (b) of formula (1) wherein $R^{10a}$ is hydrogen represent tautomeric pairs, and the tautomers are in dynamic equilibrium. It will therefore be understood that when one of the tautomers is referred to, the other is also implied.

In the case of compounds of formula (I) wherein $R^3$ combines with $R^5$ to form =O or =NOH, each compound is again produced as a racemate. Again, this is not explicityly indicated in naming these compounds, but is to be understood. These compounds are named as:

(a) trans-4,4a,5,6,7,8,8a,9-octahydro-2H-pyrazolo[3,4-g]quinolines, (b) trans-4,4a,5,6,7,8,8a,9-octahydro-1H-pyrazolo-[3,4-g]quinolines, (c) trans-5,5a,6,7,8,9,9a,10-octahydropydropyrido-[2,3-g]guinazolines, (d) trans-4,4a,5,6,7,8,8a,9-octahydrothiazolo-[4,5-g]quinolines, (e) trans-4,4a,5,6,7,8,8a,9-octahydrooxazolo-[4,5-g]quinolines, and (f) trans-4,4a,5,6,7,8,8a,9-octahydropyrrolo-[3,4-g]quinolines, Again, the 4,4a,5,6,7,8,8a,9-octahydro-1H-pyrazolo[3,4-g]quinolines and the corresponding 4,4a,5,6,7,8,8a,9 - octahydro-2H-pyrazolo[3,4,-g]quinolines of formula (1) and (2) wherein $R^{10a}$ is hydrogen represent tautomers that exist in equilibrium with each other.

The compounds of formula (1) wherein $R^3$ is OH, $NH_2$, $NHCOR^9$ or $NHSO_2NR^9R^{10}$ have an additional chiral center at the carbon atom to which the $R^3$ substituent is attached. The synthetic procedures disclosed herein allow production of two diastereomers: one composed of enantiomers (5a) and (5b), wherein the $R^3$ substituent is axial, and the other composed of enantiomers (6a) and (6b), wherein the $R^3$ substituent is equatorial.

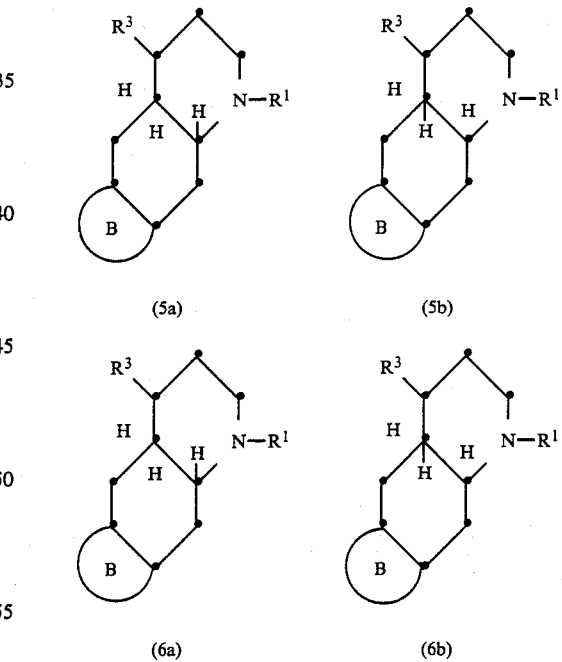

(5a)　　　　(5b)

(6a)　　　　(6b)

The racemates composed of enantiomers (5a) and (5b) are named herein by attaching the prefix rac to the name of enantiomer (5a). Enantiomer (5a) is indicated by the prefix (4aβ, 8β, 8aα), or (5aβ, 9β, 9aα) in the case of quinazolines. Accordingly, products of this type are named as:

(a) rac-(4aβ,8β,8aα)-4,4a,5,6,7,8,8a,9-octahydro-2H-pyrazolo[3,4-g]quinolines, (b) rac-(4aβ,8β,8aα)-4,4a,5,6,7,8,8a,9-octahydro-1H-pyrazolo[3,4-g]quinolines, (c) rac-(5aβ,9β,9aα)-5,5a,6,7,8,9,9a,10-octahydropyrido[2,3-g]quinazolines,
(d) rac-(4aβ,8β,8aα)-4,4a,5,6,7,8,8a,9-octahydrothiazolo[4,5-g]quinolines,
(e) rac-(4aβ,8β,8aα)-4,4a,5,6,7,8,8a,9-octahydrooxazolo[4,5-g]quinolines, and
(f) rac-(4aβ,8β,8aα)-4,4a,5,6,7,8,8a,9-octahydropyrrolo[3,4-g]quinolines.

The racemates composed of enantiomers (6a) and (6b) are named herein by prefixing rac to the name of enantiomer (6a). Enantiomer (6a) is indicated by the prefix (4aβ, 8aα, 8aα) or (5aβ, 9α, 9aα). Accordingly, products of this type are named as:

(a) rac-(4aβ,8α,8aα)-4,4a,5,6,7,8,8a,9-octahydro-2H-pyrazolo[3,4-g]quinolines,
(b) rac-(4aα,8α,8aα)-4,4a,5,6,7,8,8a,9-octahydro-1H-pyrazolo[3,4-g]quinolines,
(c) rac-(5aβ,9α,9aα)-5,5a,6,7,8,9,9a,10octahydropyrido[2,3-g]quinazolines,
(d) rac-(4aβ,8α,8aα)-4,4a,5,6,7,8,8a,9octahydrothiazolo[4,5-g]quinolines,
(e) rac-(4aβ,8α,8aα)-4,4a,5,6,7,8,8a,9-octahydrooxazolo[4,5-g]quinolines, and
(f) rac-(4aβ,8α,8aα)-4,4a,5,6,7,8,8a,9-octahydropyrrolo[3,4-g]quinolines.

Compounds having structures (2a) and (2b) are enantiomers, and are prepared as racemic mixtures by the methods discussed hereinafter. The compounds are named as:

(a) rac-(4aβ,7α,8aα)-4,4a,5,6,7,8,8a,9-octahydro2H-pyrazolo[3,4-g]quinolines,
(b) rac-(4aβ,7α,8aα)-4,4a,5,6,7,8,8a,9-octahydro-1H-pyrazolo[3,4-g]quinolines,
(c) rac-(5aβ,8α,9aα)-5,5a,6,7,8,9,9a,10-octahydropyrido[2,3-g]quinazolines,
(d) rac-(4aβ,7α,8aα)-4,4a,5,6,7,8,8a,9-octahydrothiazolo[4,5-g]quinolines,
(e) rac-(4aβ,7α,8aα)-4,4a,5,6,7,8,8a,9-octahydrooxazolo[4,5-g]quinolines, and
(f) rac-(4aβ,7α,8aα)-4,4a,5,6,7,8,8a,9-octahydropyrrolo[3,4-g]quinolines.

In each of the enantiomers the substituent R² has the axial orientation. U.S. Pat. No. 4,198,415 describes compounds having the same formula, but the racemic mixtures produced by the procedures described in that patent are ones wherein the substituent R² has the equatorial orientation.

Compounds having structures (3a) and (3b) are likewise enantiomers, and they too are prepared as racemic mixtures in the methods discussed hereinafter. These compounds are named as:

(a) rac-(5aβ,8β,9aα)-5,5a,6,7,8,9,9a,10-octahydropyrido[2,3-g]quinazolines,
(b) rac-(4aβ,7β,8aα)-4,4a,5,6,7,8,8a9-octahydrothiazolo[4,5-g]quinolines,
(c) rac-(4aβ,7β,8aα)-4,4a,5,6,7,8,8a9-octahydrooxazolo[4,5-g]quinolines.

Preparation of pyrazolo[3,4-g]quinolines

The pyrazolo[3,4-g]quinoline derivatives of formulas (1) and (2) can be prepared by reacting a 7-dimethylaminomethylene-6-oxo-trans-quinoline derivative of formula (7a) or (7b) with a compound of formula NH₂NHR¹⁰ᵃ, wherein R¹⁰ᵃ is hydrogen or (C₁-C₃)alkyl. The preparation of pyrazolo[3,4-g]quinoline derivatives of formula (1), for example, is illustrated in Reaction Scheme I:

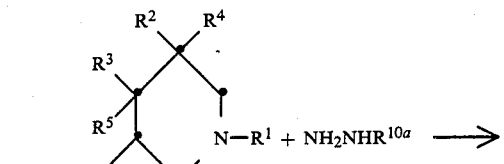

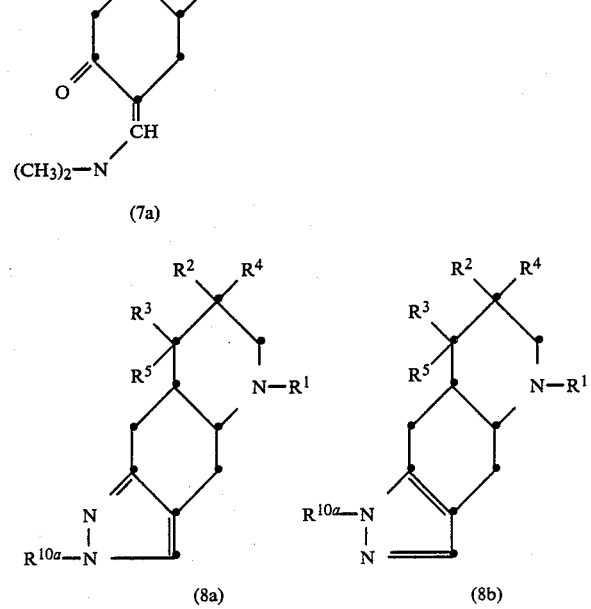

wherein R¹, R², R³, R⁴ and R⁵ are as previously defined, and R¹⁰ᵃ is hydrogen or (C₁-C₃)alkyl. The pyrazolo[3,4-g]quinolines of formulas (2) can be prepared using the same procedure with starting materials of formula (7b).

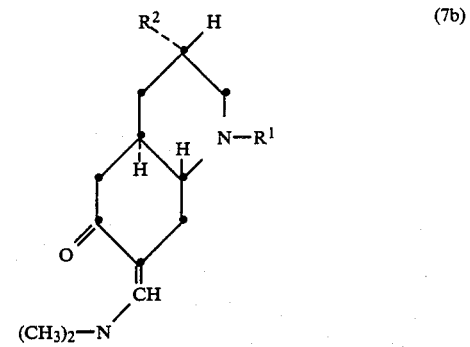

Suitable solvents for this reaction are polar organic solvents, such as C₁-C₄ alkanols, DMSO, DMF, and acetonitrile. The reaction is run at room temperature to reflux, preferably in an inert atmosphere, such as nitrogen. In each of the structures in Reaction Scheme I, as well as in the following Reaction Schemes, it should be understood that the quinoline ring system is trans fused. Preparation of pyrazolo[3,4-g]quinolines of formula (1) and (2) by the procedure of Reaction Scheme 1 is exemplified hereinafter in Examples 7, 16, 24, 26, and 28.

The pyrazolo[3,4-g]quinoline derivatives of formula (1) and (2) can also be prepared by formylating a 6-oxo-trans-quinoline derivative of formula (12a) or (12b):

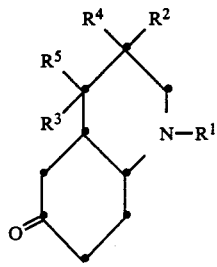 (12a)

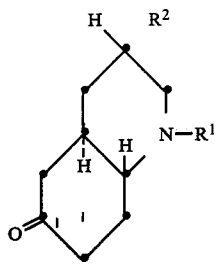 (12b)

wherein $R^1$, $R^2$, $R^3$ and $R^4$ are as previously defined, with a $(C_1-C_6)$alkyl formate, preferably ethyl formate, in the presence of base to yield the corresponding 7-formyl-6-oxo-trans-quinoline derivative. The base can be, for example, an alkali metal alkoxide or hydride, such as potassium t-butoxide or sodium hydride, or sodium ethoxide. The reaction can be carried out using a lower alkanol or similar polar anhydrous organic compound, such as THF, diethyl ether, or DMSO as solvent. THF is a preferred solvent. Although the temperature of the reaction is not critical, a range of about −20° C. to reflux may be used, with 0° C. to room temperature being preferred. The 7-formyl-6-oxo-trans-quinoline derivative thus prepared is reacted with hydrazine or a $(C_1-C_3)$ alkyl substituted hydrazine to give the products of formulas (1) and (2). This step can be carried out without isolating the 7-formyl-6-oxo-trans-quinoline intermediate. The reaction can be run at a temperature from about 0° C. to reflux, with room temperature being preferred. This process is exemplified in Examples 1, 8, 12, 18, 20, and 23.

Preparation of pyrido2,3-g]quinazolines

The pyrido[2,3-g]quinazoline derivatives of formulas (1), (2) and (3) are prepared by reacting a 7-dimethylaminomethylene-6-oxo-trans-quinoline derivative of formula (7a) or (7b), shown above, or (7c),

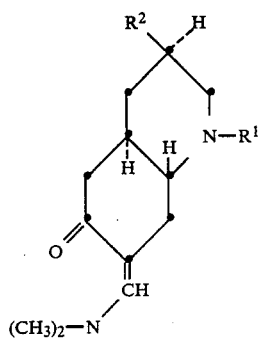 (7c)

wherein $R^1$ and $R^2$ are as defined previously, with guanidine or a guanidine derivative of formula

wherein $R^{11}$ and $R^{12}$ are independently hydrogen or $(C_1-C_3)$alkyl, as illustrated for preparation of compounds of formula (I) in Reaction Scheme II:

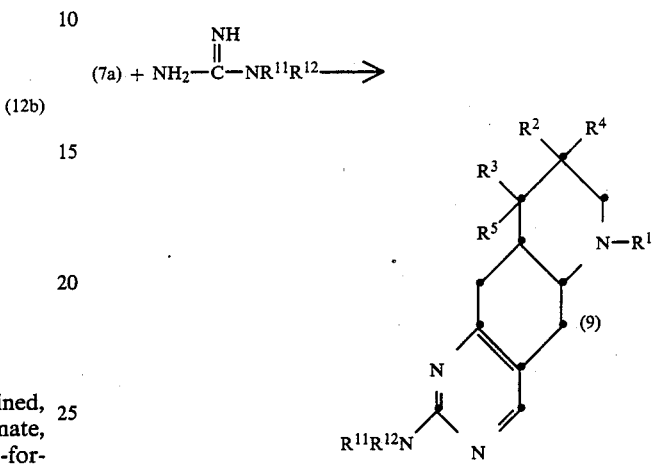

The pyrido[2,3-g]quinazolines of formulas (2) and (3) are prepared using the same procedure and starting materials of formulas (7b) and (7c) respectively. Suitable solvents are polar organic solvents, such as $(C_1-C_4)$ alkanols, DMSO, DMF, and acetonitrile. The reaction is run at room temperature to reflux, preferably in an inert atmosphere, such as nitrogen. Preparation of pyrido[3,4-g]quinazolines of formulas (1), (2) and (3) is exemplified in Examples 2, 6, 10, 11, 14, 15, 17, 25, 27, 29, and 33-35.

Preparation of pyrrolo[3,4-g]quinolines

The pyrrolo[3,4-g]quinoline derivatives of formula (1) and (2) are prepared by reacting a 7-dimethylaminomethylene-6-oxo-trans-quinoline derivative of formula (7a) or (7b) with potassium glycinate, followed by treatment of the thus formed intermediate product with acetic anhydride. This yields a 2-acetyl-pyrrolo[3,4-g]quinoline compound. The acetyl group is removed by basic hydrolysis, for example using sodium ethoxide in ethanol. Preparation of the pyrrolo[3,4-g]quinolines of formula (1) is illustrated in Reaction Scheme III:

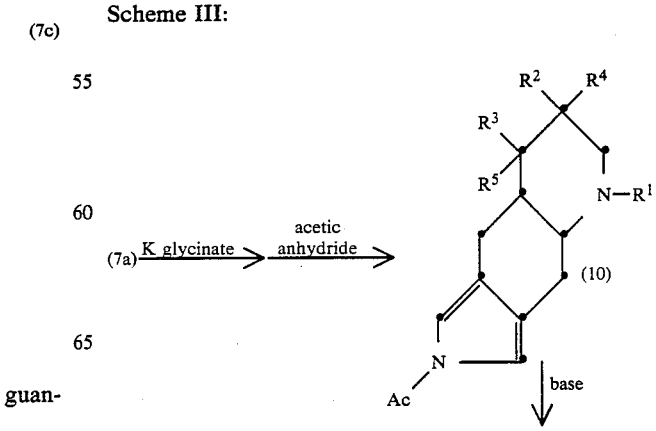

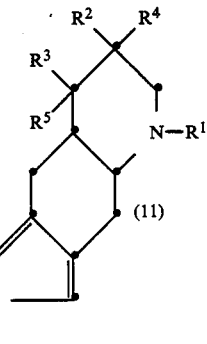

(11)

The pyrrolo[3,4-g]quinolines of formula (2) are prepared using the same procedures and starting materials of formula (7b).

Preparation of 7-dimethylaminomethylene-6-oxo-trans-quinoline intermediates

The 7-dimethylaminomethylene-6-oxo-trans-quinoline derivatives of formulas (7a), (7b), and (7c), which are sued in preparation of the pyrazolo[3,4-g]quinolines, the pyrido[2,3-g]quinolines, and the pyrrolo[3,4-g]quinolines of this invention can be prepared by reacting a 6-oxo-trans-quinoline derivative of formula (12a) or (12b), shown above, or (12c)

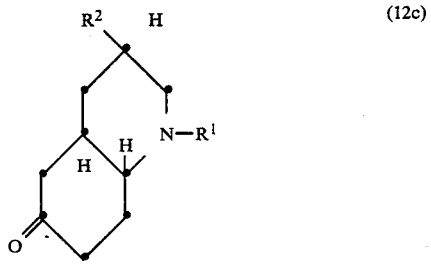

(12c)

wherein $R^1$ and $R^2$ are as previously defined, with a dimethylformamide acetal or, preferably, tris(dimethylamino)methane, as illustrated for compounds of formula (1) in Reaction Scheme IV:

Reaction Scheme IV

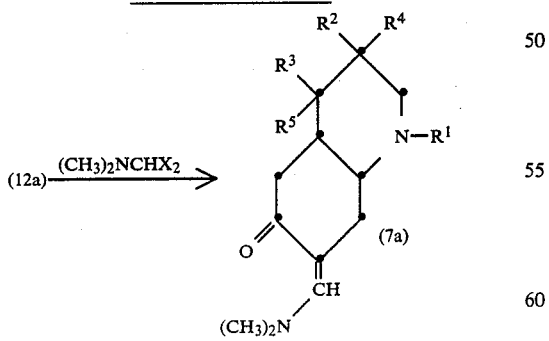

wherein $R^1$, $R^2$, $R^3$, $R^4$, and $R^5$ are as previously defined and X is —N(CH$_3$)$_2$ or OR$^{14}$ and R$^{14}$ is (C$_1$–C$_8$)alkyl, (C$_5$–C$_6$)cycloalkyl, (C$_3$–C$_4$)alkenyl, and (C$_3$–C$_4$)alkynyl.

The 7-dimethylaminomethylene-6-oxo-trans-quinoline derivatives of formulas (7a), (7b), and (7c) are preferably formed by reacting the intermediates of formulas (12a), (12b), and (12c), respectively, with tris(dimethylamino)methane in a nonpolar organic solvent such as toluene. Preparation of compounds of formulas (7a), (7b) and (7c) using this procedure is exemplified as the first step in Examples 2, 6, 7, 10, 14, 16, 17, 24, 26, and 28. It should be understood that the compounds of formulas (7a), (7b), and (7c) are prepared as racemates, although only one enantiomer is illustrated in the foregoing structures. The same is true of the intermediates of formulas (12a), (12b) and (12c).

Preparation of thiazolo[4,5-g]quinolines

The thiazolo[4,5-g]quinoline derivatives of formulas (1), (2) and (3) where $R^{13}$ is NR$^{11}$R$^{12}$ or (C$_1$–C$_3$)alkyl are prepared by reacting a 7-bromo-6-oxo-trans-quinoline derivative of formula (13a), (13b) or (13c)

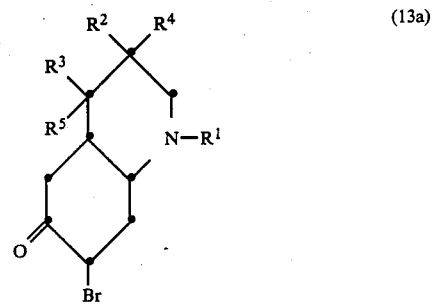

(13a)

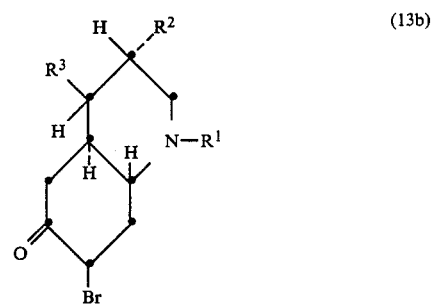

(13b)

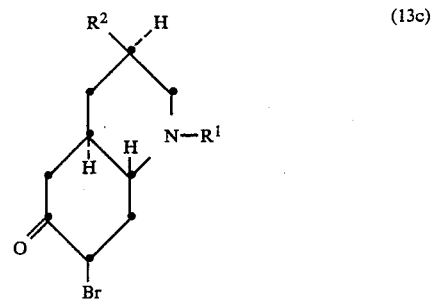

(13c)

wherein $R^1$, $R^2$, $R^3$, $R^4$, and $R^5$ are as previously defined, with a thiourea or thioamide of formula

wherein $R^{12a}$ is (C$_1$–C$_2$)alkyl or NR$^{11}$R$^{12}$ and R$^{11}$ and R$^{12}$ are as previously defined. This reaction is illustrated for compounds of formula (1) in Reaction Scheme V:

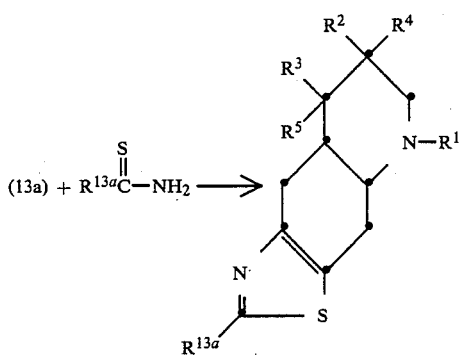

The process of Reaction Scheme V is exemplified in Examples 3, 30, and 36. Thiazolo[4,5-g]quinoline derivatives of Formulas (1), (2), and (3) wherein $R^{13}$ is hydrogen are prepared by diazotizing the primary amine group of compounds of formulas (1), (2) and (3) wherein $R^{13}$ is $NH_2$, and treating the diazonium salt with hypophosphorous acid. This process is exemplified in Examples 4, 32, and 38.

Preparation of oxazolo[4,5-g]quinolines

The oxazolo[4,5-g]quinoline derivatives of formulas (1), (2) and (3) are prepared by reacting a 7-bromo-6-oxo-trans-quinoline derivative of formula (13a), (13b) or 13c) with urea, as illustrated for compounds of formula (1) in Reaction Scheme VI:

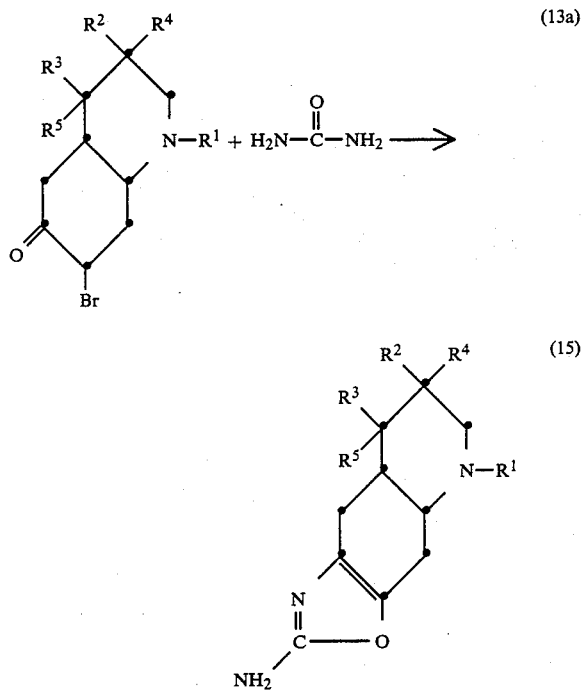

This reaction can be conducted at temperatures from 40° to 100° C. Preferred solvents are organic polar solvents such as $C_1$-$C_3$ alkanols. The oxozolo[4,5-g]quinolines of formulas (2) and (3) are prepared using the same procedure and starting materials of formulas (13b) and (13c) respectively.

Preparation of 7-bromo-6-oxo-trans-quinoline intermediates

The 7-bromo-6-oxo-trans-quinoline derivatives of formula (13) that are used in preparation of the thiazolo[4,5-g]quinoline derivatives and the oxazolo[4,5-g]quinoline derivatives of this invention can be prepared by brominating the corresponding 6-oxo-trans-quinoline derivatives of formula (12), using, for example, hydrogen bromide and bromine in glacial acetic acid, permissibly in the presence of UV light. This process is exemplified in the first step of Example 3.

Substituents $R^1$, $R^2$, $R^3$, $R^4$ and $R^5$

Compounds of formulas (1), (2), and (3) wherein $R^2$ is $CO_2R^6$ are prepared from intermediates of formulas (7) and (13) wherein $R^2$ is $CO_2R^6$ using the procedures described above, as exemplified in Examples 3, 30, and 36. Compounds of formula (1), (2), and (3) where $R^2$ is $CO_2H$ can be prepared by hydrolyzing compounds of formulas (1), (2), and (3) wherein $R^2$ is $CO_2R^{6a}$ and $R^{6a}$ is ($C_1$-$C_4$)alkyl or benzyl.

Compounds of formulas (1), (2), and (3) wherein $R^2$ is $CH_2OH$ are preferably prepared from intermediates of formulas (7) and (13) wherein $R^2$ is $CH_2OH$, as exemplified in Examples 1, 2, 12–15, 23–25, 32–33 and 38. Alternatively, compounds of formulas (1), (2), and (3) can be prepared by reducing the corresponding compound of formula (1), (2) or (3) wherein $R^2$ is $CO_2R^6$, as exemplified in Examples 5, 22, 31, and 37.

Compounds of formulas (1), (2), and (3) wherein $R^2$ is $CH_2OCH_3$ are preferably prepared from intermediates of formulas (7) and (13) wherein $R^2$ is $CH_2OCH_3$, as exemplified in Examples 6, 7, 26, 27, and 34.

Compounds of formulas (1), (2), and (3) wherein $R^2$ is —$CH_2SCH_3$ can be prepared by converting compounds of formulas (1), (2), and (3) wherein $R^2$ is —$CH_2OH$ to the corresponding chloride or bromide, and then displacing the halide with methyl mercaptide. Preferably, compounds of formulas (1), (2), and (3) wherein $R^2$ is —$CH_2SCH_3$ are prepared from intermediates of formulas (7) and (13) where $R^2$ is —$CH_2SCH_3$, as exemplified in Examples 8, 10, 28, 29, and 35.

Preparation of compounds of formulas (1), (2), and (3) wherein $R^2$ is $CH_2SOCH_3$ can be prepared by oxidizing the corresponding compound of formula (1), (2) or (3) wherein $R^2$ is $CH_2SCH_3$, as exemplified in Examples 9 and 11.

Compounds of formulas (1), (2) and (3) wherein $R^2$ is $CH_2SO_2CH_3$ can be prepared from the corresponding compounds wherein $R^2$ is $CH_2SCH_3$ or $CH_2SOCH_3$ using conventional oxidation procedures.

Compounds of formulas (1), (2) and (3) wherein $R^2$ is $CONR^7R^8$ can be prepared from the corresponding esters using conventional procedures.

Compounds of formula (1) wherein $R^3$ is hydroxy are preferably prepared from the corresponding rac-(4 α, 4aα, 8aβ)-4-hydroxy-decahydroquinolin-6-ones and rac-(4β, 4aα, 8aβ)-4-hydroxy-decahydroquinolin-6-ones of formula (12a) wherein $R^3$ is hydroxy using the procedures illustrated in the preceding Reaction Schemes, as exemplified in Examples 12–15.

Compounds of formula (1) wherein $R^3$ is $NHCOR^9$ can be prepared from the corresponding rac-(4α,4aα,-8aβ)-4-acylaminodecahydroquinolin-6-ones and rac-(4β,4aα,8aβ)-4-acylaminodecahydroquinolin-6-ones of formula (12a) using the procedures illustrated in the preceding Reaction Schemes, as exemplified in Examples 18 and 20.

Compounds of formula (1) wherein $R^3$ is $NHSO_2NR^9R^{10}$ can be obtained from the corresponding rac-(4α,4aβ,8aβ)-4-($NHSO_2NR^9R^{10}$)-decahydroquinolin-6-ones and rac-(4β, 4aα, 8aβ)-4-($NHSO_2NR^9R^{10}$)decahydroquinolin-6-ones of formula (12a) using the procedures illustrated in the foregoing Reaction Schemes, as exemplified in Examples 16 and 17.

Compounds of formula (1) wherein $R^3$ is $NH_2$ can be prepared by hydrolysis of the corresponding compound of formula (1) wherein $R^3$ is $NCOR^9$, as exemplified in Examples 19 and 21.

Compounds of formula (1) wherein $R^3$ and $R^5$ combine to form oxo are prepared by oxidizing the corresponding compound of formula (1) wherein $R^3$ is hydroxy, using conventional oxidation procedures, such as the Jones, Swern, Moffat, or Corey-Kim procedures.

Oximes of formula (1) wherein $R^3$ and $R^5$ combine to form hydroxyimino can be prepared by reacting the corresponding compound of formula (1) wherein $R^3$ and $R^5$ combine to form oxo with hydroxylamine or a salt thereof.

Compounds of formula (3) wherein $R^1$ is allyl are preferably prepared from corresponding compounds of formula (3) wherein $R^1$ is methyl or benzyl. In this procedure, the methyl or benzyl group is removed by treatment with cyanogen bromide to give an intermediate wherein $R^1$ is CN. Reductive (Zn and acetic acid) cleavage of the N-cyano compound gives the secondary amine, which is then alkylated with, for example, allyl bromide or allyl chloride.

ADDITIONAL INTERMEDIATES

The 6-oxo-trans-quinoline derivatives of formula (12), which are used to prepare the intermediates of formulas (7) and (13), also form a part of this invention. Compounds of formula (12a) wherein $R^4$ and $R^5$ combine to form a carbon-carbon bond are prepared as racemates composed of enantiomers having structures

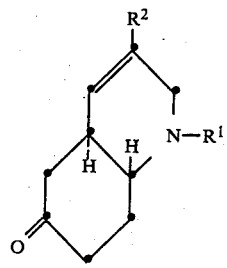

(16a)

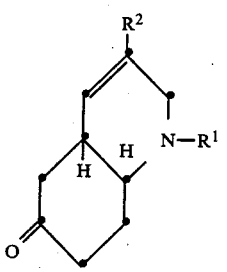

(16b)

Racemic mixtures composed of enantiomer (16a) and (16b) are named as 6-oxo-trans-1,2,4a,5,6,7,8,8a-octahydroquinolines, it being understood that the racemic mixture is intended.

Compounds of formula (12a) wherein $R^3$ is OH, $NH_2$, $NHCOR^9$ or $NHSO_2NR^9NR^{10}$, like the corresponding final products of formulas (5) and (6), have an additional chiral center at the carbon atom to which the $R^3$ substituent is attached. Accordingly, two diastereomers are possible: one composed of enantiomers (17a) and (17b), wherein the $R^3$ substituent is axial, and the other composed of enantiomers (18a) and (18b) wherein the $R^3$ substituent is equatorial.

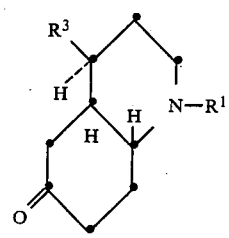

(17a)

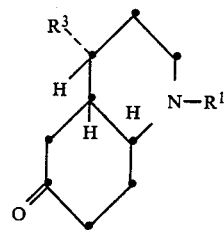

(17b)

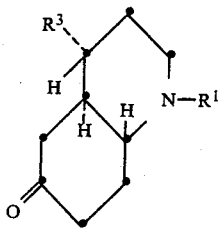

(18a)

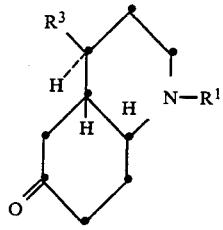

(18b)

The racemates composed of enantiomers (17a) and (17b) are named herein as rac-(4β-4aα,8aβ)-6-oxodecahydroquinolines. The racemates composed of enantiomers (18a) and (18b) are named as rac-(4α,4aα,-8α)-6-oxodecahydroquinolines.

Compounds of formula (12b) are prepared as racemic mixtures, composed of enantiomers (19a) and (19b)

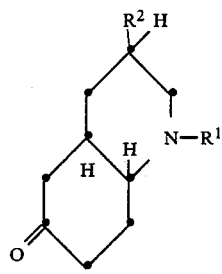 (19a)

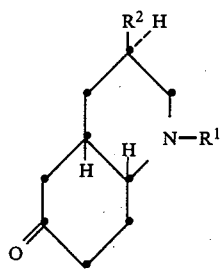 (19b)

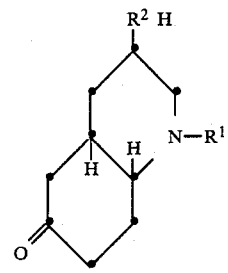 (20a)

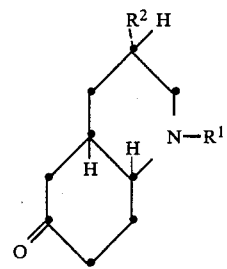 (20b)

These racemates are named herein as rac-(3α,4aα,8aβ)-6-oxodecahydroquinolines.

Compounds of formula (12c) are prepared as racemic mixtures composed of enantiomers (20a) and (20b)

These racemates are named herein as rac-(3β, 4aα,8aβ)-6-oxodecahydroquinolines.

Methods of preparing compounds of formula (16) are illustrated in Reaction Scheme VII. In the first step the 4-oxo group of a compound of formula (21), wherein $R^1$ and $R^6$ are as previously defined and $R^{15}$ and $R^{16}$ are individually ($C_1$–$C_3$)alkyl or combine to form —($CH_2$)$_n$— where n is 2–4, is reduced using, for example, sodium borohydride, to produce the corresponding alcohol of formula (22). In the second step the alcohol is converted to the corresponding mesylate of formula (23). Elimination of methanesulfonic acid from the mesylate produces the α,β-unsaturated ester of formula (24). These three steps are illustrated hereinafter in Preparation 1.

Reaction Scheme VII

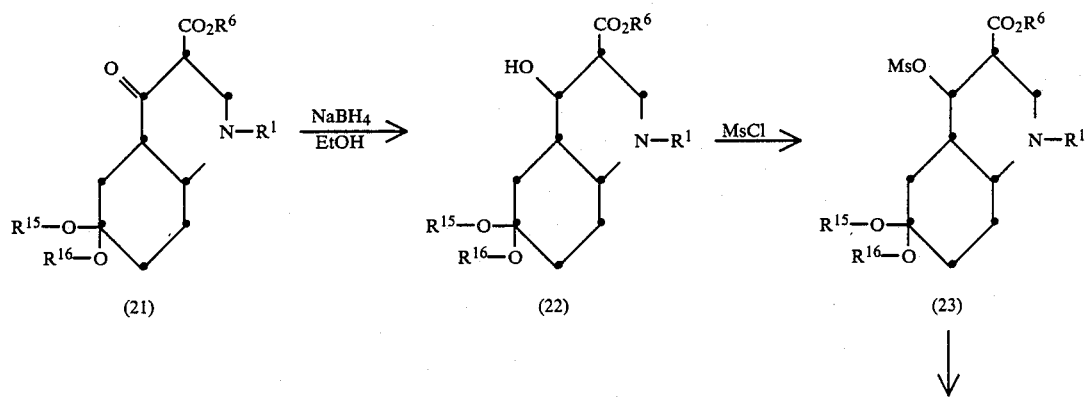

-continued
Reaction Scheme VII

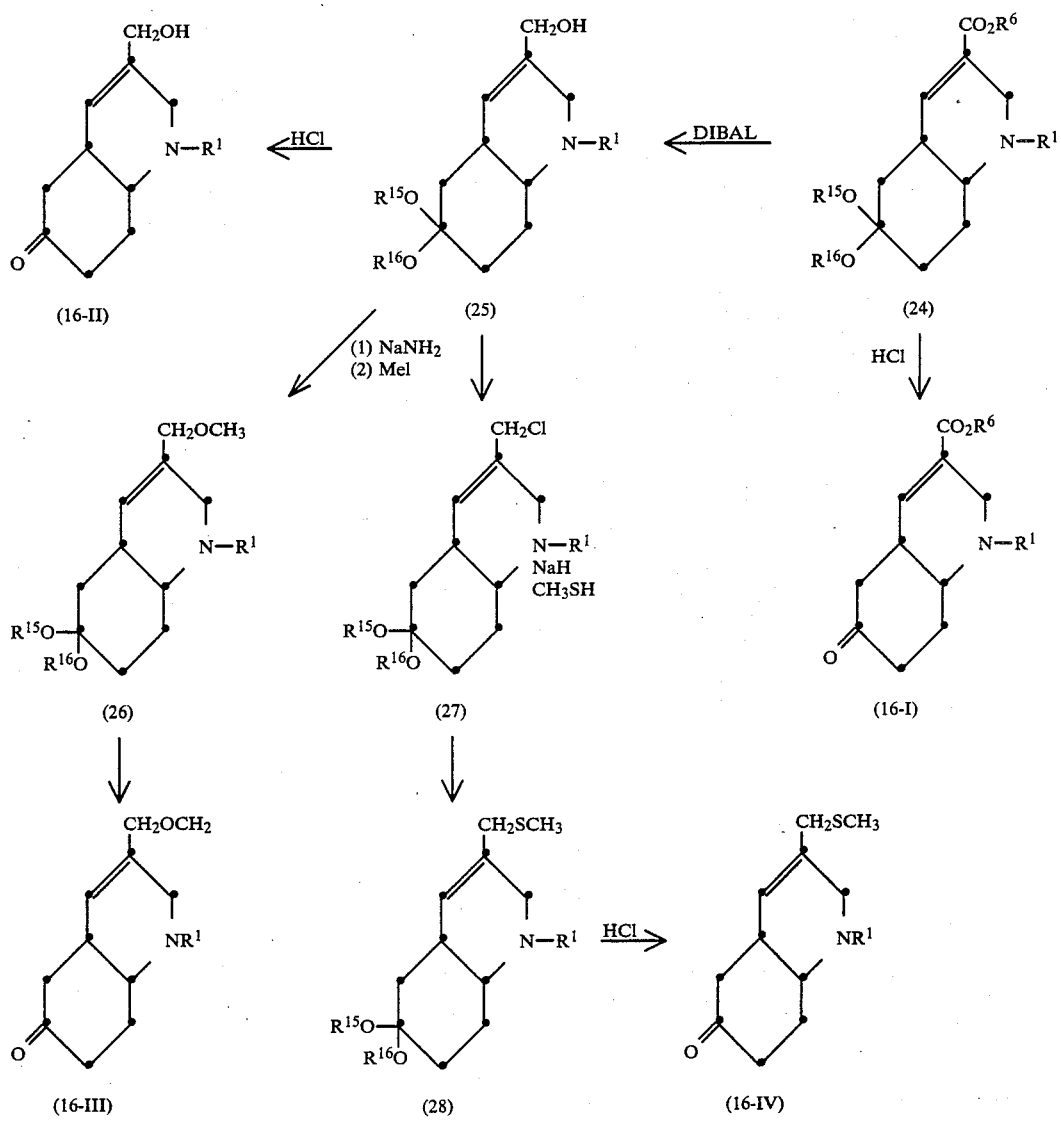

Acid hydrolysis of the α,β-unsaturated ester of formula (24), using hydrochloric acid for example, produces the 6-oxo-1-substituted-trans-1,2,4a,5,6,7,8,8a-octahydroquinoline of formula (16-I), which is useful in preparing compounds of formula (4) wherein $R^2$ is $CO_2R^6$. The acid hydrolysis step is exemplified hereinafter in Preparation 3.

Reduction of the α,β-unsaturated ester of formula (24) using diisobutylaluminum hydride produces the corresponding allylic alcohol of formula (25). Acid hydrolysis of the acetal portion of the compound of formula (25) produces the 3-(6-oxo-1-substituted-trans-1,2,4a,5,6,7,8,8a-octahydroquinoline)methanol of formula (16-II), which is useful in preparing compounds of formula (4) wherein $R^2$ is $CH_2OH$. Preparation 2 exemplifies conversion of a compound of formula (24) to one of formula (16-II).

Deprotonation of the allylic alcohol of formula (25) using a strong base such as sodium amide, followed by treatment with methyl iodide produces the 3-methoxymethyl-1-substituted-trans-1,2,4a,5,6,7,8,8a-octahydro-quinoline-6-one acetal of formula (26), which is hydrolyzed with hydrochloric acid to provide the ketone of formula (16-III). These steps are exemplified in Preparation 4.

The allylic alcohol of formula (25) is chlorinated, preferably using triphenylphosphinedichloride, to produce the intermediate and formula (27). Treatment of this intermediate with methanethiol in the presence of a strong base such as sodium hydride produces the 3-methylthiomethyl compound of formula (28), which upon acid hydrolysis gives the 3-methylthiomethyl-6-oxo-1-substituted trans-1,2,4a,5,6,7,8,8a-octahydroquinoline of formula (16-IV). These steps are exemplified in Preparation 5.

Reaction Scheme VIII

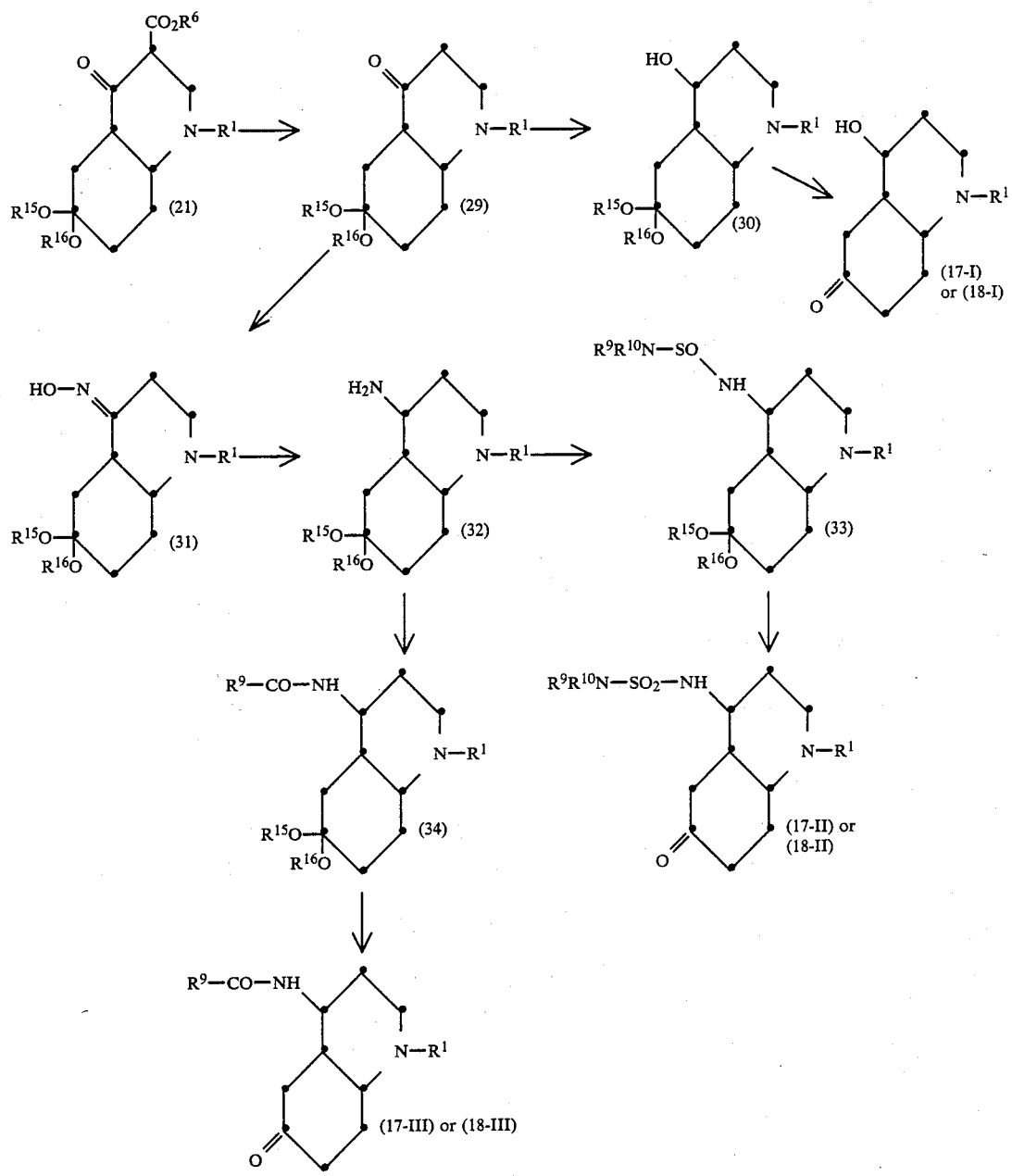

Methods of preparing compounds of formulas (17) and (18) are illustrated in Reaction Scheme VIII. The starting material of formula (21) is decarboxylated, using, for example, 10% potassium hydroxide, as illustrated in Preparation 6, to produce the intermediate of formula (29). Reduction of the 4-oxo group of the intermediate of formula (29) with L-Selectride ® (lithium tri-sec-butylborohydride, 1.0M in tetrahydrofuran) produces a compound of formula (30) that, on acid hydrolysis, gives the rac-(4β,4aα,8aβ)-4-(6-oxo-1-substituted-decahydroquinolin)-ol of formula (17-I). This reaction is illustrated in Preparation 8. Reduction of the 4-oxo group of the intermediate of formula (29) with lithium in ammonia produces a compound of formula (30) that, on acid hydrolysis, gives the rac-(4α,4aα,8aβ)-4-(6-oxo-1-(substituted)decahydroquinolin)-ol of formula (18-I). This reaction is illustrated in Preparation 7.

Reacting the ketone of formula (29) with hydroxylamine produces the oxime of formula (31). Reduction of the oxime with lithium aluminum hydride produced a 1:1 mixture of the rac-(4α,4aα,8aβ) and rac-(4β, 4aα,-8aβ)-6-oxo-1-substituted-decahydroquinolin-4-amine acetal racemates of formula (32). The two diastereomers can be separated on a silica gel column. This preparation is illustrated in Preparation 9.

The 4-alkanoylamino and 4-aminosulfonylamino derivatives of formulas (17) and (18) are prepared from the 4-amino compounds without affecting the stereo-chemistry of the compounds. Accordingly, the rac-(4β, 4aα,-8aβ)-4-alkanoylamino-6-oxo-1-substituted-decahydroquinoline acetal racemates of formula (17-III) are prepared by acylating the acetal of the corresponding rac-(4β,4aα,8aβ)-6-oxo-1-substituted-decahydroquinolin-4-amine, and hydrolyzing the resulting compounds of formula (34). This is illustrated in Preparation 12. The rac-(4α,4aα,8aβ)-4 alkanoylamino-6-oxo-1-substituted-decahydroquinoline acetal racemates of formula (18-III) are prepared in the same way, starting with the rac-(4α,4aα,8aβ)-4-amine compound of formula (32) as illustrated in Preparation 11.

Similarly, sulfonylation of the appropriate racemate of the 4-amino compound of formula (32) with a compound of the formula $R^9R^{10}NSO_2Cl$, produces the corresponding racemate of formula (33), which on acid hydrolysis produces the corresponding racemate of formula (17-II) or (18-II), as illustrated in Preparation 10 for the (4α,4aα,8aβ) racemate.

reaction is exemplified in Preparation 13. Acid hydrolysis of the intermediate of formula (35) produces the rac-(3α,4aα,8aβ)-3-(6-oxo-1-substituted-decahydroquinoline)methanols of formula (19-II). This reaction is exemplified in Preparation 14. rac-(3α,4aα,8aβ)-3-Methoxymethyl-6-oxo-1-substituted-decahydroquinolines of formula (19-III) are prepared using methods exemplified in Preparation 15. rac-(3α,4aα,8aβ)-3-Methylthiomethyl-6-oxo-1-substituted-decahydroquinolines of formula (19-IV) are prepared using methods exemplified in Preparation 16.

The rac-(3α,4aα,8aβ)-6-oxo-1-substituted-decahydroquinoline-3-carboxylic acid esters of formula (19)

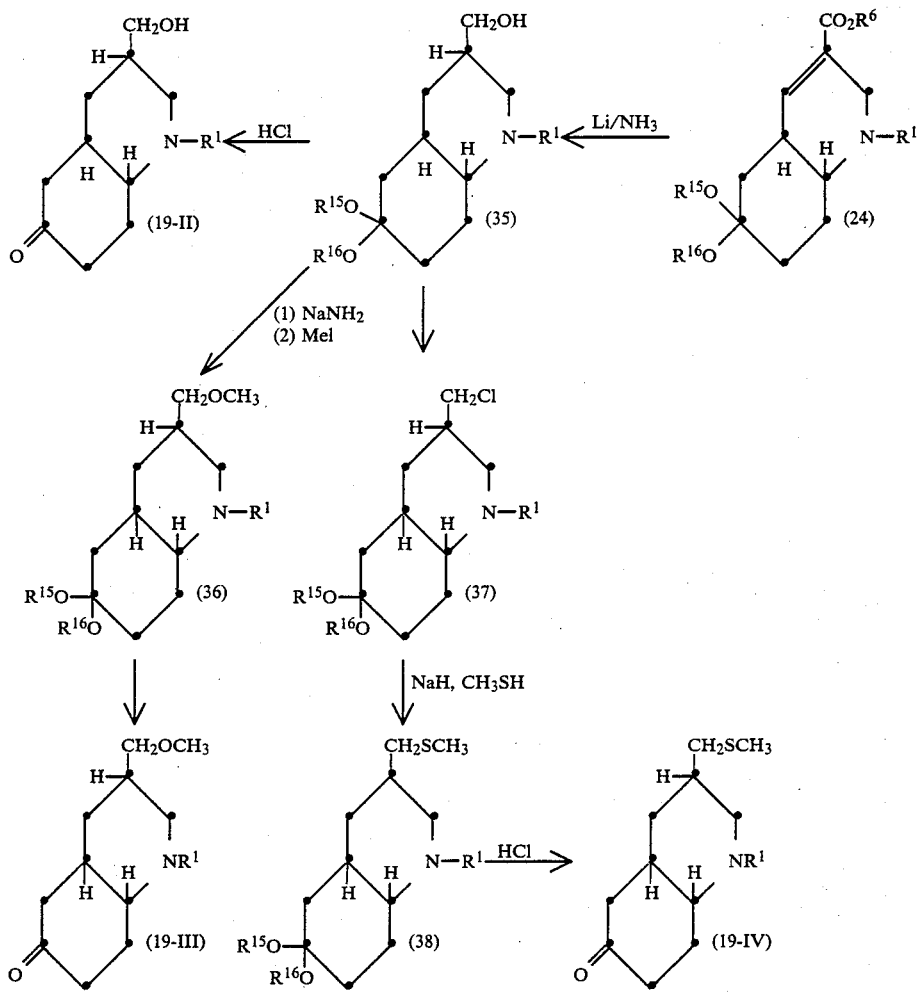

Reaction Scheme IX

Preparation of racemates of formula (19), which are useful in preparing final-products of formula (2), is illustrated in Reaction Scheme IX. In the first 2 step, the α,β-unsaturated ester of formula (24) is reduced using lithium in ammonia to produce the rac-(3α,4aα,8aβ)-3-(4-oxo-1-substituted-decahydroquinoline)methanol acetal of formula (35) (only one enantiomer is shown). This wherein $R^2$ is $CO_2R^6$ can be prepared by oxidizing the corresponding alcohol of formula (19-II) to provide the carboxylic acid of formula (19) wherein $R^2$ is $CO_2H$, and then esterifying. Alternatively, the esters of formula (19) wherein $R^2$ is $CO_2R^6$ can be obtained by epimerizing the acetal of the diastereomeric ester, as described below.

Reaction Scheme X

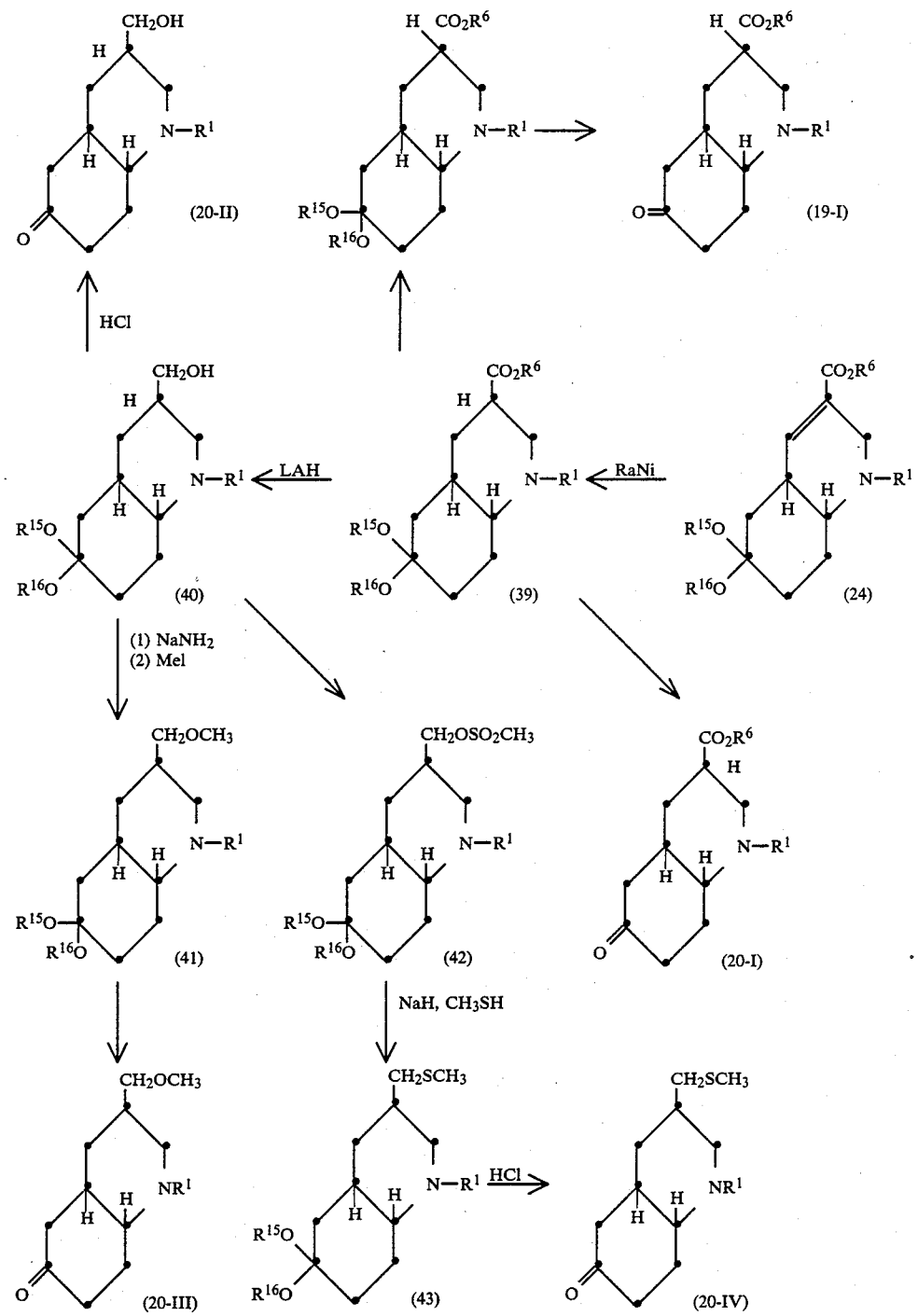

Preparation of racemates of formula (20), is illustrated in Reaction Scheme X. These intermediates are useful in preparation of compounds of formula (3). In the first step, the α,β-unsaturated ester of formula (24) is hydrogenated using Raney ® nickel as catalyst, to produce the acetal of rac-(3β,4aα,8aβ)-6-oxo-3-substituted-decahydroquinoline-3-carboxylic acid ester of formula (39). This reaction is illustrated in Preparation 19. Hydrolysis of the acetal of formula (39) gives the corresponding ketone of formula (20-I), as exemplified in Preparation 24. Reducing the carboxylic acid ester function of the acetal of formula (39) using lithium aluminum hydride gives the corresponding alcohol of formula (40) as exemplified in Preparation 20. The (3β,4aα,8aβ) alcohol of formula (40) is converted to the intermediate of formula (20-II) (Preparation 21), formula (20-III) (Preparation 22), and formula (20-IV) Preparation 23), using the procedures previously discussed. In each case, the procedures used do not affect the configuration of the carbon atom to which the $R^2$ substituent is attached.

The rac-(3β,4aα,8aβ) esters of formula (39) can be epimerized to provide the corresponding (3α,4aα,8aβ) esters by treating the esters of formula (39) with lithium diisopropylamide, followed by protonation as illustrated in Preparation 17. This intermediate can then be hydrolyzed to provide rac-(3α,4aα,8aβ)-(6-oxo-1-substituted-decahydroquinoline-3-carboxylic acid ester of formula (19-I)

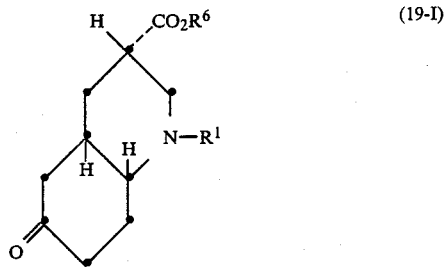

as exemplified in Preparation 18.

The intermediates of formula (21) in Reaction Scheme VII are prepared by the process illustrated in Reaction Scheme XI, wherein $R^{15}$ and $R^{16}$ are $C_1-C_3$ alkyl or combine to form $-(CH_2)_n-$ where n is 2-4, and $R^{17}$ is methyl or ethyl, and $R^1$ and $R^6$ are as defined previously. These reactions are exemplified in Preparations 25-29 and Example 39. The intermediates of formula (21) also form a part of the invention.

Reaction Scheme XI

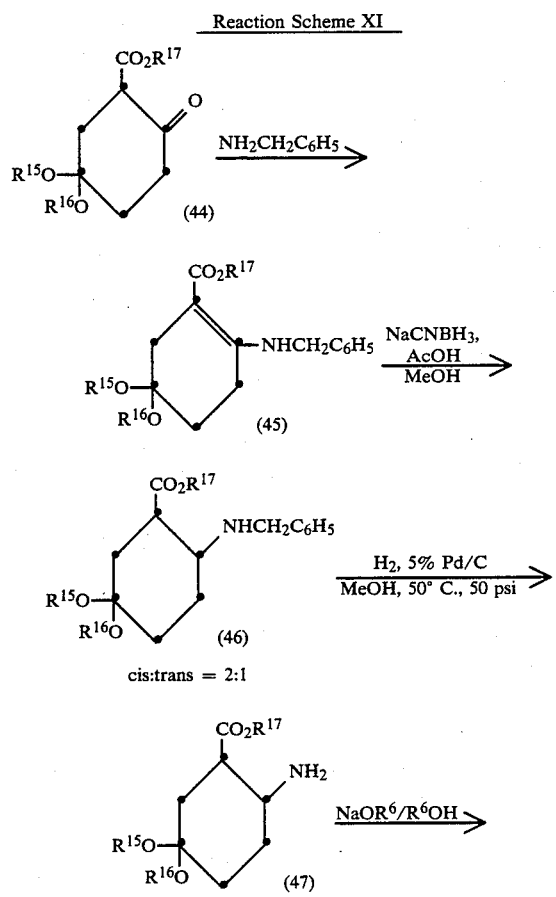

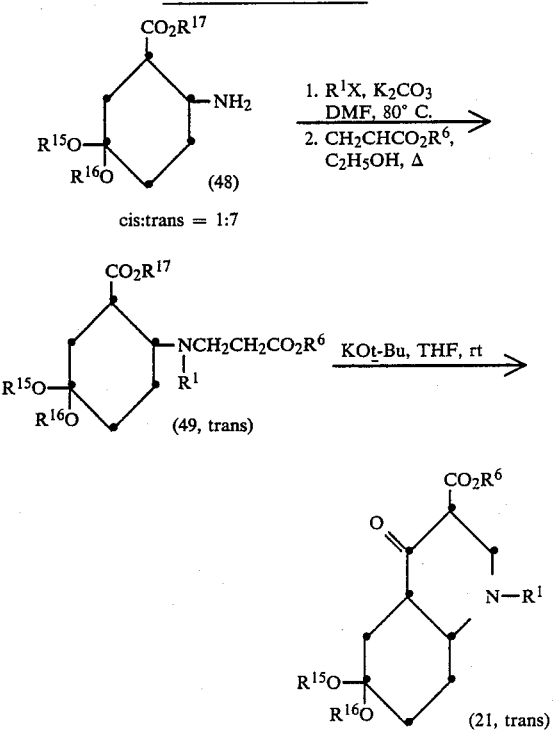

The intermediates of formula (44) in Reaction Scheme XI are prepared by the method described by Pariza, et al., *Synthetic Communications*, 13, 243 (1983).

The invention is further illustrated by the following Preparations and Examples.

PREPARATION 1

Ethyl 1'-propyl-trans-spiro[1,3-dioxolane-2,6'-(1',2',-4a',5',6',7',8',8a'-octahydroquinoline)]-3'-carboxylate

A. Reduction of ethyl 4-oxo-1-propyl-trans-spiro[decahydroquinoline-6,2'-(1',3'-dioxolane)]-3-carboxylate A solution of 63.3 g (0.2 mole) of ethyl 4-oxo-1-propyl-trans-spiro[decahydroquinoline-6,2'-(1',3'-dioxolane)]-3-carboxylate in 500 ml of ethanol was cooled to 0° C. To this was added a solution comprising 2.4 g (0.06 mole) of sodium borohydride (NaBH₄) in 500 ml of ethanol. The mixture was stirred for 15 minutes at 0° C., then it was poured into water. The product was extracted into methylene chloride, which was then dried using sodium sulfate and evaporated to give 64.1 g of product represented by four spots on TLC. This was passed through a silica gel column with EtOAc/hexane (1:2), followed by EtOAc containing a trace of NH₄OH. The fractions containing the two compounds represented by the TLC spots with the higher $R_f$'s were combined to give 17.1 g of product (hereinafter designated as Sample 1). The fractions containing the two compounds represented by the TLC spots with lower $R_f$'s were combined to give 45.9 of product (hereinafter designated as Sample 2).

Samples 1 and 2 were composed of different isomers of ethyl 4-hydroxy-1-propyl-trans-spiro[decahydroquinoline-6,2'-(1',3'-dioxolane)]-3-carboxylate. The two samples were reacted separately in the following steps B and C.

B. Sulfonylation of ethyl 4-hydroxy-1-propyl-trans-spiro[decahydroquinoline-6,2'-(1',3'-dioxolane)]3-carboxylate Sample 1 of ethyl 4-hydroxy-1-propyl-trans-spiro[decahydroquinoline-,6,2'-(1',3'-dioxolane)]-3-carboxylate (17.1 g, 0.05 mole) from step A was dissolved in 100 ml of pyridine. Then 9.0 g (0.078 mole) of methanesulfonyl chloride was added to the mixture, and this was stirred overnight. The pyridine was evaporated to give a brown foam identified as ethyl 4-methylsulfonyloxy-1-propyl-trans-spiro[decahydroquinoline-6,2'-(1',3'-dioxolane)]-3-carboxylate (Sample 1). This was carried over for use in step C.

Sample 2 of ethyl 4-hydroxy-1-propyl-trans-spiro[decahydroquinoline-6,2'-(1',3'-dioxolane)]-3carboxylate from step A (45.9 g, 0.14 mole) was sulfonylated using the foregoing procedure, except that three times the relative amount of methanesulfonyl chloride was used, to produce a black foam identified as ethyl 4-methylsulfonyloxy-1-propyl-trans-spiro[decahydroquinoline-6,2'-(1',3'-dioxolane)]-3-carboxylate (Sample 2).

C. Elimination of methanesulfonic acid from ethyl 4-methylsulfonyloxy-1-propyl-trans-spiro-[decahydroquinoline-6,2'-(1',3'-dioxolane)]-3-carboxylate To a solution of Sample 1 of ethyl 4-methylsulfonyloxy-1-propyl-trans-spiro-[decahydroquinoline6,2'-(1',3'-dioxolane)]-3-carboxylate (from step B) in 150 ml of ethanol was added 100 ml of a 1N solution of sodium ethoxide in ethanol The mixture was stirred at room temperature overnight. Then another 100 ml of the 1N ethoxide solution was added, and this was stirred overnight. The mixture was then poured onto ice, and the hydrogen ion concentration was adjusted to pH 10. The product was extracted into methylene chloride, and the resulting methylene chloride solution was dried with sodium sulfate and evaporated to give 19.2 g of a dark brown oil. This was passed through a silica gel column with hexane/THF (4:1) containing a trace of NH4OH. Fractions shown by TLC to contain ethyl 1'-propyl-trans-spiro[1,3-dioxolane-2,6'-(1',2',4a',5',6',7',8',8a'octahydroquinoline)]-3'-carboxylate were combined to give 10.5 g.

Later fractions were combined to give 1.4 g of a mixture comprising the desired product and an impurity. This mixture was passed through a silica gel column with hexane/THF (3:1) containing a trace of NH4OH. Fractions shown by TLC to contain ethyl 1'-propyl-trans-spiro[1,3-dioxolane-2,6'-(1',2',4a',5',6',7',8',8a'-octahydroquinoline)]-3'-carboxylate were combined to give 0.8 g of material, making a total of 11.3 g (Sample 1).

Sample 2 of ethyl 4-methylsulfonyloxy-1-propyl-trans-spiro[decahydroquinoline-6,2'-(1',3'-dioxolane)]-3-carboxylate from step (B) was subjected to the same process as above, except that one half the relative amount of sodium ethoxide and one half the reaction time was used, producing 18.3 g of ethyl 1'-propyltrans-spiro[1,3-dioxolane-2,6'-(1',2',4a',5',6',7'8',8a'-octahydroquinoline)-3'-carboxylate.

PREPARATION 2

3-Hydroxymethyl-1-propyl-trans-1,2,4a,5,6,7,8,8a-octahydroquinolin-6-one

A. Reduction of ethyl 1'-propyl-trans-spiro[1,3-dioxolane-2,6'-(1',2',4a',5',6',7',8',8a'-octahydroquinoline)]-3'-carboxylate To a solution of 2.2 g (7.1 mmole of ethyl 1'-propyl-trans-spiro[1,3-dioxolane-2,6'-1',2',4a',5',-6',7',8',8a'-octahydroquinoline)]-3'-carboxylate in toluene (100 ml) at 0° C., 17.8 ml of a 1M solution of diisobutylaluminum hydride in methylene chloride was added slowly. After stirring 10 minutes, 100 ml of methanol was added and the mixture was stirred at room temperature for 45 minutes. The precipitate was removed by filtering the mixture through a pad of celite.

The filtrate was evaporated and the residue passed through a silica gel column with 5% MeOH/CH2Cl2 containing a trace of NH4OH. The fractions shown by TLC to contain 3'-(1'-propyl-trans-spiro[1,3-dioxolane-2,6'-(1',2',4a',5',6',7',8',8a'-octa-hydroquinoline)]methanol were combined to give 1.5 g of an oil which solidified upon setting.

B. Hydrolysis of 3'-(1'-propyl-trans-spiro[1,3-dioxolane-2,6'-(1',2',4a',5',6',7',8',8a'-octahydroquinoline)])methanol A solution of 1.6 g of 3'-(1'-propyl-trans-spiro-[1,3-dioxolane-2,6'-(1',2',4a',5',6',7',8',8a'octahydroquinoline)])methanol in 100 ml of water and 20 ml of concentrated hydrochloric acid was prepared and stirred for 1 hour. It was then poured into a water and ice mixture. The resulting mixture was made basic. Then the product was extracted into a solution of CHCl3/i-PrOH (3:1), which was evaporated to give 1.3 g of 3-hydroxymethyl-1-propyl-trans-1,2,4a,5,6,7,8,8a-octahydroquinolin-6-one.

EXAMPLE 1

7-(5-Propyl-trans-4,4a,5,6,8a,9-hexahydro-2H-pyrazolo[3,4-]quinoline)methanol

A solution of 1.8 g (15.7 mmole) of potassium tert-butoxide in 20 ml of THF was cooled to 0° C. To this was added a solution of 1.3 g (5.8 mmole) of 3-hydroxymethyl-1-propyl-trans-1,2,4a,5,6,7,8,8a-octahydroquinolin-6-one (Preparation 2), 1.7 g (23.3 mmole) of ethyl formate, and 40 ml of THF. The mixture was warmed to room temperature and stirred for 3 hours, after which 4 ml of hydrazine was added and the hydrogen ion concentration was adjusted to pH 9–10. The mixture was stirred overnight at room temperature and, then poured into water. The product was extracted into a solution of CHCl3/i-PrOH (3:1), which was then evaporated to give 1.3 g of a brown gum. This was purified on a silica gel column with 10% MeOH/CH2Cl2 containing a trace of NH4OH, yielding 400 mg of material, which was dissolved in CHCl3. A solid crystallized out of the solution, and hexane was added to increase crystallization of the product. The crystals were separated by filtration, providing 390 mg of material identified as a trichloromethane complex of the title compound M.P. 112–115° C.

Analysis Calcd:   C, 49.08;   H, 6.05;   N, 11.51,   Cl, 29.00

| Found: | C, 49.46; | H, 5.67; | N, 11.33, | Cl, 28.83 |

Mass spectrum: 246, 218, 152, 118.

EXAMPLE 2

8-(2-Amino-6-propyl-trans-5,5a,6,7,9a,10-hexahydropyrido[2,3-q]quinazoline)methanol To a solution of 1.5 g (6.7 mmole) of 3-hydroxymethyl-1-propyl-trans-1,2,4a,5,6,7,8,8a-octahydroquinolin-6-one (Preparation 2) in 100 ml of toluene there was added 4.5 ml (16.9 mmole) of tris(dimethylamino)methane. The mixture refluxed for 1 hour. The toluene was evaporated to give a brown oil. To a solution of this material in 75 ml of ethanol was added a suspension of 1.2 g (6.7 mmole) of guanidine carbonate in 75 ml of ethanol. The mixture was heated to reflux for 3 hours, allowed to stand at room temperature overnight, and was then poured into water. The product was extracted from the aqueous mixture into $CHCl_3$/i-PrOH (3:1). The organic solvent was evaporated, giving a brown semi-solid product, which was put in a vacuum desiccator overnight. The resulting product weighed 1.9 g. It was passed through a silica gel column with 10% $MeOH/CH_2Cl_2$ containing a trace of $NH_4OH$. The fractions shown by TLC to contain the product were combined to give 0.5 g of a yellow solid. This was taken up in a mixture of methanol and methylene chloride. The solution was boiled down and ethyl acetate was added until crystals began to form. The solution was cooled and the solid collected by filtration and dried in a vacuum desiccator, giving 0.4 g of the title product.

| Analysis Calcd: | C, 65.67; | H, 8.08; | N, 20.42 |
| Found: | C, 65.44; | H, 7.80; | N, 20.29 |

Mass spectrum: 287, 273, 245, 198, 166, 152, 122.
Infrared spectrum (KBr): 3380, 3316, 3192, 1642, 1593, 1562, 1476, 1030 $cm^{-1}$.

PREPARATION 3

Ethyl 6-oxo-1-propyl-trans-1,2,4a,5,6,7,8,8a-octahydroquinoline-3-carboxylate A solution comprising 4.0 g (26 mmole) of ethyl 1'-propyl-trans-spiro[1,3-dioxolane-2,6'-(1',2',4a',5',6',7',8',8a'-octahydroquinoline)]-3'-carboxylate (4.0 g) (Preparation 1), 40 ml of concentrated HCl, and 100 ml of water was stirred at room temperature for one hour, and then poured onto ice. The hydrogen ion concentration was adjusted to pH 10, and the product was extracted into a solution of $CHCl_3$/i-PrOH (3:1), which was then dried with sodium sulfate and evaporated to give 3.5 g of the title product.

EXAMPLE 3

Ethyl 2-amino-5-propyl-trans-4,4a,5,6,8a,9-hexahydrothiazolo[4,5-g]quinoline-7-carboxylate A solution comprising 3.5 g (13 mmole) of ethyl 6-oxo-1-propyl-trans-1,2,4a,5,6,7,8,8a-octahydroquinoline-3-carboxylate (Preparation 3), 100 ml of acetic acid and 5.2 g (20 mmole) of a 31% solution of hydrogen bromide in acetic acid was prepared. 2.5 g (16 mmole) of bromine was slowly added, and the mixture was stirred at room temperature for 15 minutes. The acetic acid was then stripped off, and the residue was taken up in ethanol. To this solution 1.1 g (15 mmole) of thiourea was added, and the mixture was refluxed for 4 hours. The mixture was then cooled to room temperature, and poured into water. The product was extracted into a solution of $CHCl_3$/i-PrOH (3:1), which was then dried with sodium sulfate and evaporated to give 4.3 g of product. This was passed through a silica gel column with 5% $MeOH/CH_2Cl_2$ containing a trace of $NH_4OH$. The fractions shown by TLC to contain the title compound were combined to give 2.6 g of material.

Proton nmr ($CDCl_3$) 90 MHz: 6.70 (s, 1H), 4.15 (q, 2H), 1.30 (t, 3H), 0.90 (t, 3H).

EXAMPLE 4

Ethyl 5-propyl-trans-4,4a,5,6,8a,9-hexahydrothiazolo[4,5-g]quinoline-7-carboxylate A solution of 0.5 g (1.5 mmole) of ethyl 2-amino-5-propyl-trans-4,4a,5,6,8a,9-hexahydrothiazolo-[4,5-g]quinoline-7-carboxylate (Example 3) in 50 ml of 85% phosphoric acid was cooled to 0° C. Then 110 mg (1.8 mmole) of sodium nitrite dissolved in as small an amount of water as possible was slowly added under the surface of the reaction mixture. The resulting mixture was added dropwise to 50 ml of 50% hypophosphorous acid ($H_3PO_2$) at 0° C. The mixture was stirred at room temperature until gas evolution ceased. This took about 1 hour. The mixture was poured onto ice, and the hydrogen ion concentration of the mixture was adjusted to pH 11. Water was added to dissolve the precipitate that formed; then the product was extracted into a solution of $CHCl_3$/i-PrOH (3:1). This solution was dried using sodium sulfate and evaporated to give 0.46 g of the title product.

Proton nmr ($CDCl_3$) 90 MHz: 8.52 (s, 1H), 6.79 (s, 1H), 4.18 (q, 2H), 1.32 (t, 3H), 0.92 (t, 3H).

EXAMPLE 5

7-(5-Propyl-trans-4,4a,5,6,8a,9-hexahydrothiazolo-[4,5-g]quinoline)methanol

To a solution comprising 0.46 g (1.6 mmole) of ethyl 5-propyl-trans-4,4a,5,6,8a,9-hexahydrothiazolo-[4,5-g]quinoline-7-carboxylate (Example 4) in 100 ml of THF at 0° C., there was added 7.8 ml (7.8 mmole) of a 1M solution of diisobutylaluminum hydride in methylene chloride. To this mixture, 100 ml of methanol was added, and the resulting mixture was stirred for 1 hour. The precipitate was removed by filtering the mixture through a pad of celite. The filtrate was evaporated, and the residue was passed through a silica gel column with 5% $MeOH/CH_2Cl_2$ containing a trace of $NH_4OH$, providing the title compound. This was converted to the dihydrochloride salt, which was then recrystallized from MeOH/EtOAc to give a tan solid, M.P. >235° C., identified as 7-(5-propyl-trans-4,4a,5,6,8a,9-hexahydrothiazolo-[4,5-g]quinoline)-methanol dihydrochloride.

Mass spectrum: m/e=264.

PREPARATION 4

3-Methoxymethyl-1-propyl-trans-1,2,4a,5,6,7,8,8a-octahydroquinolin-6-one

A. Methylation of 3'-(1'-propyl-trans-spiro[1,3'dioxolane-2,6'-(1',2',4a',5',6',7',8',8a'-octahydroquinoline)]methanol Ammonia (300 ml) was distilled into a flask through a BaO column. First sodium metal (580 mg, 25.3 mmole) and then a trace of $FeCl_3$ were added to the ammonia. 3'-(1'-propyl-trans-spiro[1,3-dioxolane-2,6'-(1',2',4a',5',6',7',8',8a'-octahydroquinoline)])methanol (2.7 g, 10.1 mmole) was added, and the mixture was stirred for 3 hours. Methyl iodide (4.3 g, 30.3 mmole) was added to the mixture, which was then stirred an additional 2 hours. The mixture was then added to water. The product was extracted into methylene chloride, which was then dried with sodium sulfate and evaporated to give 2.9 g of product. This was run through a silica gel column with 3% $MeOH/CH_2Cl_2$ containing a trace of $NH_4OH$. The fractions shown by TLC to contain 3-methoxymethyl-1'-propyl-trans-spiro-[1,3-dioxolane-2,6'-(1',2',4a',5',6',7',8',8a'-octahydroquinoline)] were combined to give 2.2 g of product.

B. Hydrolysis of 3'-methoxymethyl-1'-propyl-trans-spiro[1,3-dioxolane-2,6'-(1',2',4a',5',6',7',8',8a'-octahydroquinoline)]

A solution of 2.2 g of 3'-methoxymethyl-1'-propyl-trans-spiro[1,3-dioxolane-2,6'-(1',2',4a',5',6',7',8',8a'-octahydroquinoline)] in 100 ml of water and 20 ml of concentrated hydrochloric acid was prepared and stirred for 1 hour. It was then poured onto ice. The hydrogen ion concentration was adjusted to pH 10, and the product extracted into a solution of $CHCl_3$/i-PrOH (3:1). This was dried with sodium sulfate and evaporated to give 1.9 g of 3'-methoxymethyl-1-propyl-trans-1,2,4a,5,6,7,8,8a-octahydroquinolin-6-one.

EXAMPLE 6

8-(Methoxymethyl)-6-propyl-trans-5,5a,6,7,9a,10-hexhydropyrido[2,3-g]quinazolin-2-amine The title product was prepared using the procedure of Example 2 and the compound of Preparation 4 as starting material.

| Analysis Calcd: | C, 66.64; | H, 8.39; | N, 19.43 |
|---|---|---|---|
| Found: | C, 66.76; | H, 8.20; | N, 19.52 |

Mass spectrum: 287, 259, 243, 198, 166, 136.

EXAMPLE 7

7-(Methoxymethyl)-5-propyl-4,4a,5,6,8a,9-trans-hexahydro-2H-pyrazolo[3,4-g]quinoline To a solution of 850 mg (3.6 mmole) of 3-methoxymethyl-1-propyl-trans-1,2,4a,5,6,7,8,8a-octahydroquinolin-6-one in 50 ml of toluene was added 1.3 g (9.0 mmole) of tris(dimethylamino)methane. This refluxed for 2 hours, then the toluene was evaporated and the residue was taken up in 50 ml of ethanol. To this, 2 ml of hydrazine was added, and the resulting mixture was stirred overnight at room temperature. The mixture was poured into water and the product was extracted into methylene chloride. The methylene chloride solution was dried using sodium sulfate and evaporated to give 950 mg of a light brown oil. This was passed through a silica gel column with 5% $MeOH/CH_2Cl_2$ containing a trace of $NH_4OH$. The fractions shown by TLC to contain the title compound were combined to give a yellow oil, which crystallized on setting. This was recrystallized from EtOAc/hexane to give 550 mg of the title compound.

| Analysis Calcd: | C, 68.93; | H, 8.87; | N, 16.08 |
|---|---|---|---|
| Found: | C, 68.99; | H, 8.64; | N, 16.11 |

Mass spectrum: 260, 232, 216, 166, 136.

PREPARATION 5

3-Methylthiomethyl-1-propyl-trans-1,2,4a,5,6,7,8,8a-octahydroquinolin-6-one

A. Conversion of 3'-(1'-propyl-trans-spiro[1,3-dioxolane-2,6'-(1',2',4a',5',6',7',8',8a'-octahydroquinoline)]methanol to the corresponding allylic chloride Chlorine gas was bubbled through a solution of 7.5 g (28.5 mmole) of triphenylphosphine in 75 ml of tetrachloromethane until the solution began to turn yellow. The tetrachloromethane was then evaporated, and the white solid residue was dissolved in 100 ml of DMF. To this solution was added a solution of 3.8 g (14.2 mmole) of 3'-(1'-propyl-trans-spiro[1,3-dioxolane-2,6'-(1',2',4a',5',6',7',8',8a'-octahydroquinoline)])methanol, and the resulting mixture was stirred for 1½ hours at room temperature, resulting in a solution of 3'-chloromethyl-1'-propyl-trans-spiro[1,3-dioxolane2,6'-(1',2',4a',5',6',7',8',8a'-octahydroquinoline)]in DMF.

B. Substitution of methyl mercaptide for chloride in 3'-chloromethyl-1'-propyl-trans-spiro[1,3-dioxolane-2,6'-(1',2',4a',5',6',7',8',8a'-octahydroquinoline)]

To 19.2 ml of methanethiol solution (3.5M in DMF) at 0° C. was added 2.2 g of a 60% dispersion of sodium hydride in mineral oil. To this was added a solution of 1.6 g (5.6 mmole) of 3'-chloromethyl-1'-propyl-trans-spiro[1,3-dioxolane-2,6'-(1',2',4a',5',6',7',8', 8a'-octahydroquinoline)]in 10 ml of DMF. The mixture was allowed to warm to room temperature and was stirred for 3 hours, after which it was poured into water. The product was extracted into methylene chloride, which was then dried with sodium sulfate and evaporated to give 2.6 g of product. This was passed through a silica gel column with 5% $MeOH/CH_2Cl_2$. The fractions shown by TLC to contain 3'-methylthiomethyl-1'-propyl-trans-spiro-[1,3-dioxolane-2,6'-(1',2',4a',5',6',7',8'-8a'-octahydroquinoline)]were combined to give 1.7 g of product.

C. Hydrolysis of 3'-methylthiomethyl-1'-propyl-trans-spiro[1,3-dioxolane-2,6'-(1',2',4a',5',6',7',8',8a'-octahydroquinoline)]

A solution comprising 2.6 g of 3'-methylthiomethyl-1'-propyl-trans-spiro[1,3-dioxolane-2,6'-(1',2',4a',5',6',7',8',8a'-octahydroquinoline)] in 100 ml of water and 40 ml of concentrated HCl was stirred at room temperature for 1 hour. The mixture was then poured over ice, and made basic with 50% sodium hydroxide. The product was extracted into a solution of $CHCl_3$/i-PrOH (3:1), which was evaporated to give 2.2 g of 3-methylthiomethyl-1-propyl-trans-1,2,4a,5,6,7,8,,8a-octahydroquinolin-6-one.

EXAMPLE 8

7-(Methylthiomethyl)-5-propyl-trans-4,4a,5,6,8a,9-hexahydro-2H-pyrazolo[3,4-g]quinoline The title compound was prepared using the process of Example 1 and the compound of Preparation 5 as starting material. M.P. 133°–134° C.

| Analysis Calcd: | C, 64.94; | H, 8.36; | N, 15.15; | S, 11.56 |
|---|---|---|---|---|
| Found: | C, 65.26; | H, 8.26; | N, 14.91; | S, 11.30 |

Mass spectrum: 276, 248, 230, 182, 136, 94.

Infrared spectrum (CHCl$_3$): 3466, 3240, 2964, 1375, 1136.

Proton nmr (CDCl$_3$) 270 MHz: 7.34 (s, 1H), 5.46 (s, 1H), 2.02 (s, 3H), 0.93 (t, 3H).

EXAMPLE 9

7-(Methylsulfinylmethyl)-5-propyl-trans-4,4a,5,6,8a,9-hexahydro-2H-pyrazolo[3,4-g]quinoline To a solution of 480 mg (1.7 mmole) of 7-(methylthiomethyl)-5-propyl-trans-4,4a,5,6,8a,9-hexahydro-2H-pyrazolo[3,4-g]quinoline (Example 8) in 50 ml of methanol was added a solution of 740 mg (3.5 mmole) of sodium metaperiodate in 20 ml of water. The mixture was stirred for 1 hour at room temperature and then poured into water. The hydrogen ion concentration was adjusted to pH 11, and then the product was extracted into a solution of CHCl$_3$/i-PrOH (3:1). The solvent was evaporated to give 0.47 g of product, which was passed through a silica gel column with 7–10% MeOH/CH$_2$Cl$_2$ tr NH$_4$OH. The fractions shown by TLC to contain the title compound were combined to give 230 mg of a foam.

Proton nmr (CDCl$_3$) 270 MHz: 7.34 (s, 1H), 5.72 (s, 1H), 2.62 (s, 3H), 0.93 (t, 3H).

Mass spectrum: 292, 261, 247, 230, 218, 200, 170, 152, 136.

EXAMPLE 10

8-(Methylthiomethyl)-6-propyl-trans-5,5a,6,7,9a,10-hexahydropyrido[2,3-g]quinazolin-2-amine The title compound was made using the procedure of Example 2 and the compound of Preparation 5 as starting material.

Mass spectrum: 303, 275, 257, 227, 213, 198, 182.

Infrared spectrum (CHCl$_3$): 3422, 2936, 1607, 1562, 1457.

Proton nmr (CDCl$_3$) 270 MHz: 8.08 (s, 1H), 5.48 (s, 1H), 4.89 (s, 2H), 2.01 (s, 3H), 0.94 (t, 3H).

The maleate salt was made of a 400 mg portion of the title compound. The salt was recrystallized from MeOH/EtOAc, producing 270 mg of product, which was then dissolved in warm MeOH. Activated carbon was added and the mixture was filtered while hot. The residue was recrystallized to give 90 mg of the maleate salt of the title compound as yellow crystals.

| Analysis Calcd: | C, 57.12; | H, 6.71; | N, 13.32 |
|---|---|---|---|
| Found: | C, 57.35; | H, 6.84; | N, 13.32 |

EXAMPLE 11

8-(Methylsulfinylmethyl)-6-propyl-trans-5,5a,6,7,9a,10-hexahydropyrido[2,3-g]quinazolin-2-amine The title compound was prepared following the procedure of Example 9 and using the compound of Example 10 as the starting material.

Proton nmr (DMSO$_{d6}$) 270 MHz: 8.02 (s, 1H), 5.64 (s, 1H), 2.32 (s, 3H), 0.87 (t, 3H).

Mass spectrum: 273, 256, 245, 227, 152, 136.

PREPARATION 6

1-Propyl-trans-spiro[decahydroquinoline-6,2'-(1',3'-dioxolan)]-4-one

A solution of 30.0 g of ethyl 4-oxo-1-propyl-trans-spiro[decahydroquinoline-6,2'-(1',3'-dioxolane)]-3-carboxylate in 180 ml of methanol was prepared. To this was added 120 ml of a 10% solution of potassium hydroxide in methanol. The mixture refluxed overnight, and was then cooled to room temperature and poured onto ice. The product was extracted into methylene chloride, which was then dried with sodium sulfate and evaporated to give 22.1 g of a yellow oil. (Yield 94.6%)

PREPARATION 7 rac-(4β,4aα,8aβ)-4-Hydroxy-1-propyl-decahydroquinolin-6-one

A. Stereoselective reduction of 1-propyl-trans-spiro-[decahydroquinoline-6,2'-(1',3'-dioxolan)]-4-one A solution comprising 19.8 ml (19.8 mmole) of L-Selectride® (a 1.0M solution of lithium tri-sec-butylborohydride in tetrahydrofuran) and 100 ml of tetrahydrofuran was cooled to −78° C. To this solution was slowly added a solution of 2.5 g (9.9 mmole) of 1-propyl-1-trans-spirodecahydroquinoline-6,2'-(1',3'-dioxolan)]-4-one (Preparation 6). The resulting mixture was stirred for 45 minutes. Water was then added until gas evolution ceased. Then approximately 2 g of trimethylamine-N-oxide was added, and the mixture was stirred for 2½ hours. The mixture was then poured into water, and it was confirmed that the mixture was basic. The product was extracted into methylene chloride, which was then dried with sodium sulfate and evaporated to give a red oil. This was passed through a silica gel column with 10% MeOH/CH$_2$Cl$_2$ to give 1.5 g of an orange oil that was identified as rac-(4β,4aα,8aβ)-1-propylspiro[decahydroquinoline-6,2'-(1',3'-dioxolan)]-4-ol.

B. Hydrolysis of rac-(4β,4aα,8aβ)-1-propylspiro[decahydroquinoline-6,2'-(1',3'-dioxolan)]-4-ol A solution comprising 1.5 g of rac-(4β,4aα,8aβ)-1-propylspiro[decahydroquinoline-6,2'-(1',3'-dioxolan)]-4-ol, 20 ml of concentrated hydrochloric acid, and 100 ml of water was prepared and stirred for 1 hour at room temperature. The mixture was then made basic while cooled. The product was extracted into CHCl$_3$/i-PrOH (3:1), which was then dried with sodium sulfate and evaporated to give 1.1 g of a light brown solid that was identified as rac-(4α,4aα,8aβ)-4-hydroxy-1-propyl-decahydroquinolin-6-one. (Yield 88.6%).

PREPARATION 8 rac-(4α,4aα,8aβ)-4-Hydroxy-1-propyldecahydroquinolin-6-one

A. Stereoselective reduction of 1-propyl-trans-spiro-[decahydroquinoline-6,2'-(1',3'-dioxolan)]-4-one To a solution formed by adding 0.75 g (10.8 mmole) of lithium metal to 500 ml of ammonia there was slowly added a solution comprising 9.1 g (36 mmole) of 1-propyl-trans-spiro[decahydroquinoline-6,2'-(1',3'-dioxolan)]-4-one (Preparation 6), 2.7 g (3.4 ml) of t-butyl alcohol, and 100 ml of THF. The mixture was stirred for 30 minutes, and then water was added dropwise until the color disappeared. Most of the ammonia was evaporated, and the residue was poured into water. The product was extracted into methylene chloride, which was dried with sodium sulfate and evaporated to give 9.1 g of a brown gum. This was passed through a silica gel column with 5% MeOH/CH$_2$Cl$_2$ containing a trace of NH$_4$OH, followed by 10% MeOH/CH$_2$Cl$_2$ when the product was mostly off. The fractions shown by TLC to contain the same compound were combined to provide 4.9 g of an amber oil, which was identified as rac-(4α,4aα,8β)-1-propylspiro[decahydroquinoline-6,2'-(1',3'-dioxolan)]-4-ol.

Hydrolysis of rac-(4α,4aα,8aβ)-1-propylspiro[decahydro-quinoline-6,2'-(1',3'-dioxolan)]-4-ol.

A solution comprising 3.8 g of rac-(4α,4aα,8aβ)-1-propylspiro[decahydroquinoline-6,2'-(1',3'-dioxolan)-4-ol, 40 ml of concentrated HCl, and 200 ml of water was prepared and stirred for 1 hour at room temperature. The mixture was then poured onto ice and made basic with NaOH. The product was extracted into methylene chloride, which was then dried using sodium sulfate, and evaporated to give 3.5 g of an amber oil, which was identified as rac-(4α,4aα,8aβ)-4-hydroxy-1-propyl-decahydroquinolin-6-one.

EXAMPLE 12 rac-(4aβ,8β,8aα)-5-Propyl-4,4a,5,6,7,8,8a,9-octahydro-2H-pyrazolo[3,4-g]quinolin-8-ol A solution of 1.4 g (12.8 mmole) of potassium tert-butoxide in 20 ml of tetrahydrofuran was prepared and cooled to 0° C. To the solution were added 1.0 g (4.7 mmole) of rac-(4β,4aα,8aβ)-4-hydroxy-1-propyl-decahydroquinolin-6-one (Preparation 7), 1.4 g (19.0 mmole) of ethyl formate, and 20 ml of tetrahydrofuran. The mixture was stirred at room temperature for 1 hour, forming a slurry. Then 3 ml of hydrazine was added, the hydrogen ion concentration was adjusted to pH 9, and the mixture was stirred for an additional 2 hours. The mixture was poured onto ice, and the product was extracted into methylene chloride, which was dried with sodium sulfate and evaporated to give 400 mg of product. Additional product left in the aqueous layer was extracted into a solution of CHCl$_3$/i-PrOH (3:1), which was dried with sodium sulfate and evaporated to give 680 mg of product. The combined lots were run through a silica gel column with 20% MeOH/CH$_2$Cl$_2$ containing a trace of NH$_4$OH. The fractions shown by TLC to contain the product were combined to give 850 mg. The free base was recrystallized from MeOH-/EtOAc providing 270 mg of the title product as a white powder. M.P. 153°–154° C.

Mass spectrum: 235, 219, 206, 159, 119, 107

UV spectrum (EtOH): $\lambda_{max}$=222 nm

Proton nmr (CDCl$_3$) 270 MHz: 7.34 (s, 1H), 4.34 (d, 1H), 0.88 (t, 3H).

Infrared spectrum (CHCl$_3$): 3450, 3225, 2947, 2875, 1078.

EXAMPLE 13 rac-(4aβ,8α,8aα)-5-Propyl-4,4a,5,6,7,8,8a,9-octahydro-2H-pyrazolo[3,4-g]quinolin-8-ol The title product was produced using the process of Example 12 and the product of Preparation 8 as starting material.

Infrared spectrum (CHCl$_3$): 3470, 3234, 1450, 1084 cm$^{-1}$.

Proton nmr (CDCl$_3$) 270 MHz: 7.28 (d, 1H), 0.89 (t, 3H).

Mass spectrum: 235, 206, 140, 124.

EXAMPLE 14 rac-(4aβ,8β,8aα)-2-Amino-6-propyl-5,5a,6,7,8,9,9a,10-octahydropyrido[2,3-g]quinazolin-9-ol methanesulfonate (1:2)

To a solution of 1.1 g (5.2 mmole) of rac-(4β,4aα,8aβ)-4-hydroxy-1-propyldecahydroquinolin-6-one (Preparation 7) in 60 ml of toluene was added 1.9 g (13.0 mmole) of tris(dimethylamino)methane. The mixture refluxed for 1 hour, and was then evaporated to a brown residue. This was mixed with 50 ml of ethanol, and the mixture was added to a suspension of 0.95 g (5.2 mmole) of guanidine carbonate in 50 ml of ethanol. The mixture was refluxed for 4 hours, then cooled, and poured into water. The product was extracted into a solution of CHCl$_3$/i-PrOH (3:1), which was then dried with sodium sulfate and evaporated to give 1.3 g of a dark yellow gum. This was passed through a silica gel column with 10% MeOH/CH$_2$Cl$_2$containing a trace of NH$_4$OH. The fractions shown by TLC to contain the wanted material were combined to give 0.63 g of a yellow solid. A salt was obtained by adding methanesulfonic acid and recrystallizing from MeOH/EtOAc, to provide 450 mg of the title product as a yellow powder. M.P. 238°–239° C.

Infrared spectrum (KBr): 3304, 3165, 2954, 1661, 1602, 1569, 1496 cm$^{-1}$.

Mass spectrum: 261, 244, 234, 215, 153.

EXAMPLE 15 rac-(4aβ,8α,8aα)-2-Amino-6-propyl-5,5a,6,7,8,9,9a,10-octahydropyrido[2,3-g]quinazolin-9-ol dihydrochloride The free base of the title compound was prepared using the procedure of Example 14 and the compound of Preparation 8 as the starting material.

Mass spectrum: 262, 244, 234, 215, 153.

Infrared spectrum (KBr): 3380, 3320, 3166, 2980, 1653, 1599, 1565, 1487 cm$^{-1}$.

Proton nmr (CDCl$_3$, DMSO$_{d6}$) 270 MHz: 8.00 (s, 1H), 0,90 (t, 3H).

UV spectrum (EtOH): $\lambda_{max}$=229.

The hydrochloride salt was then formed. M.P. 296°–298° C.

---

Analysis Calcd: C, 50.15; H, 7.22; N, 16.71; Cl, 21.15

-continued

| Found: | C, 50.36; | H, 7.45; | N, 16.76; | Cl, 21.15 |

PREPARATION 9 rac-(4α,4aα,8aβ)-1-Propyl-spiro[decahydroquinoline-6,2'-(1',3'-dioxolan)]-4-amine and rac-(4β,4aα,8aβ)-1-propyl-spiro[decahydroquinoline-6,2'-(1',3'-dioxolan)]-4-amine

A. Addition of hydroxylamine to 1-propyl-trans-spiro-[decahydroquinoline-6,2'-(1',3'-dioxolan)]-4-one To a solution of 1.3 g (5.1 mmole) of 1-propyl-trans-spiro[decahydroquinoline-6,2'-(1',3'-dioxolan)-]4-one was added 1.0 g (13.9 mmole) of hydroxylamine hydrochloride. The mixture was stirred overnight at room temperature, then poured into water. The product was extracted into methylene chloride, which was then dried with sodium sulfate and evaporated to give 1.4 g of a tan solid, which was identified as 1-propyl-trans-spiro[decahydroquinoline-6,2'-(1',3'-dioxolan)]-4-one oxime.

B. Reduction of 1-propyl-trans-spiro[decahydroquinoline-6,2'-(1',3'-dioxolan)]-4-one oxime A solution of 3.2 g (12 mmole) of 1-propyl-trans-spiro[decahydroquinoline-6,2'-(1',3'-dioxolan)]-4-one oxime in 50 ml of tetrahydrofuran was slowly added to a suspension of 1.0 g (26 mmole) of lithium aluminum hydride in 50 ml of tetrahydrofuran, and the mixture was refluxed for 2 hours. Then 1 ml of water, 1 ml of 15% sodium hydroxide in water, followed by an additional 3 ml of water were added, and the resulting mixture was stirred for a further 30 minutes. Then the precipitate was filtered off through a pad of celite. The filtrate was evaporated to give 2.8 g of product, which was run through a silica gel column with THF/MeOH (3:1) containing a trace of $NH_4OH$. The fractions shown by TLC to contain the higher $R_f$ material were combined to give 0.97 g of rac-(4β,4aα,8aβ)-1-propyl-spiro[decahydroquinoline-6,2'-(1',3'-dioxolan)]-4-amine. The fractions shown by TLC to contain the lower $R_f$ material were combined to give 0.8 g of rac-(4α,4aα,8aβ)-1-propylspiro[decahydroquinoline-6,2'-(1',3'-dioxolan)]-4-amine. The fractions shown by TLC to contain both materials were combined to give 0.5 g of a mixture of the two isomers.

PREPARATION 10 rac-(4α,4aα,8aβ)-4-(Dimethylaminosulfonylamino)-1-propyldecahydroquinolin-6-one

A. Sulfonylation of rac-(4α,4aα,8aβ)-1-propylspiro-[decahydroquinoline-6,2'-(1',3'-dioxolan)]-4-amine To a solution of 3.6 g (14 mmole) of rac-(4α,4aα,8aβ)-1-propylspiro[decahydroquinoline-6,2'-(1',3'-dioxolan)]-4-amine in 100 ml of methylene chloride there was added 175 mg (1.4 mmole) of 4-dimethylaminopyridine and 7.2 g (71 mmole) of triethylamine. To this mixture was added 2.4 g (17 mmole) of dimethylsulfamoyl chloride, and the mixture was stirred 4 hours at room temperature. Then an additional 2.4 g (17 mmole) of dimethylsulfamoyl chloride and 7.2 g (71 mmole) of triethylamine were added and the mixture was stirred overnight at room temperature. The mixture was then poured into water and the product was extracted into methylene chloride, which was then dried using sodium sulfate and evaporated to give 3.8 g of product. This was passed through a silica gel column with 5% MeOH/$CH_2Cl_2$ containing a trace of $NH_4OH$. The fractions shown by TLC to contain rac-(4α,4aα,8aβ)-4-(dimethylaminosulfonylamino)-1-propyl-spiro[decahydroquinoline-6,2'- (1',3'-dioxolane)]were combined to give 2.3 g of product.

B. Hydrolysis of rac-(4α,4aα,8aβ)-4-(dimethylaminosulfonylamino)-1-propylspiro[decahydroquinoline-6,2'-(1',3'-dioxolane)].

A solution of 2.3 g (6.4 mmole) of rac-(4α,4aα,8aβ)-4-(dimethylaminosulfonylamino)-1-propyl-spiro[decahydroquinoline-6,2'-(1',3'-dioxolane)] in 100 ml of formic acid was prepared and stirred overnight at room temperature. The mixture was then poured onto ice and the hydrogen ion concentration of the resulting mixture was adjusted to pH 10. Product was extracted into a solution of $CHCl_3$/i-PrOH (3:1), which was then dried using sodium sulfate to give 2.1 g of rac-(4α,4aα,8aβ)-4-(dimethylaminosulfonylamino)-1-propyl-trans-decahydroquinolin-6-one.

EXAMPLE 16 rac-(4aβ,8α,8aα)-8-(Dimethylaminosulfonylamino)-5-propyl-4,4a,5,6,7,8,8a,9-octahydro-2H-pyrazolo[3,4-g]quinoline ethanolate To a solution of 1.0 g (3.1 mmole) of rac-(4a,4aα,8aβ)-4-(dimethylaminosulfonylamino)-1-propyl-trans-decahydroquinolin-6-one (Preparation 10) in 100 ml of toluene was added 1.1 g (7.9 mmole) of tris(dimethylamino)methane. The mixture was refluxed for 45 minutes, then the toluene was removed and the residue was taken up in 100 ml of ethanol. To this, 3 ml of hydrazine was added, and the mixture was stirred overnight at room temperature. The mixture was poured into water. The product was extracted into methylene chloride, which was then dried with sodium sulfate and evaporated to give 1.1 g of product. This was passed through a silica gel column with 7→10% MeOH/$CH_2Cl_2$ containing a trace of $NH_4OH$. The fractions shown by TLC to be the product were combined to give a yellow foam.

Mass spectrum: m/e=341.
UV; $\lambda_{max}$=6278.3.

This was recrystallized from EtOH/$Et_2O$ to give 360 mg of the title solvate.

| Analysis Calcd: | C, 52.69; | H, 8.58; | N, 18.07 |
| Found: | C, 52.44; | H, 7.28; | N, 18.02 |

EXAMPLE 17 rac-(5aβ,8α,8aα)-9-(Dimethylaminosulfonylamino)-6-propyl-trans-5,5a,6,7,9,9a,10-octahydropyrido[2,3-g]quinazolin-2-amine To a solution of 1.1 g (3.5 mmole) of rac-(4α,4aα,8aβ)-4-(dimethylaminosulfonylamino)-1-propyldecahydroquinolin-6-one (Preparation 10) in 100 ml of toluene was added 1.3 g (8.7 mmole) of tris(dimethylamino)methane. This was refluxed for 45 minutes. The toluene was removed and the residue was taken up in 100 ml of ethanol. To this, 250 mg (4.2 mmole) of guanidine was added, and the mixture was stirred at room temperature overnight. Then another 240 mg (4.2 mmole) of guanidine was added, and the mixture was heated at 50° C. for 2 hours, after which it was poured into water. The product was extracted into a solution of $CHCl_3$/i-PrOH (3:1), which was then dried using sodium sulfate and evaporated to give 1.2 g of product. This was run through a silica gel column with 5% $MeOH/CH_2Cl_2$ containing a trace of $NH_4OH$. The fractions shown by TLC to contain the product were combined to provide 0.9 g of material, which was recrystallized from EtOH/$E_2O$ to give 380 mg of the ethanol solvate of the title compound.

UV spectrum (EtOH): $\lambda_{max}=229$, $\epsilon=14,180$.
Mass spectrum: m/e=368.

When heated at 110° C. the solvate decomposed and the ethanol was driven off leaving the title compound.

| Analysis Calcd: | C, 52.15; | H, 7.66; | N, 22.81 |
|---|---|---|---|
| Found: | C, 52.33; | H, 7.57; | N, 22.65 |

M.P. 201° C. (decomposed).

PREPARATION 11 rac-(4α,4aα,8aβ)-4-Acetylamino-1-propyldecahydroquinolin-6-one

A. Acylation of rac-(4α4aα,8aβ)-1-propylspiro[decahydroquinoline-6,2'-(1',3'-dioxolan)]-4-amine To a solution of 1.4 g (5.5 mmole) of rac-(4α,4aα,8aβ)-1-propylspiro[decahydroquinoline-6,2'-(1',3'-dioxolan)]-4-amine in 50 ml of pyridine was added 67 mg (0.55 mmole) of 4-dimethylaminopyridine and 1.4 g (13.8 mmole) of triethylamine. The mixture was cooled to 0° C. and 0.5 g (6.6 mmole) of acetyl chloride was added. The mixture was warmed to room temperature, stirred overnight, and poured into water. The product was extracted into methylene chloride, which was then dried using sodium sulfate and evaporated to give 1.5 g of product. This was passed through a silica gel column with 5% $MeOH/CH_2Cl_2$ containing a trace of $NH_4OH$. The fractions shown by TLC to contain rac-(4α,4aα,8aβ)-4-acetylamino-1-propylspiro[decahydroquinoline-6,2'-(1',3'-dioxolane)] were combined to give 1.15 g of a white solid.

B. Hydrolysis of rac-(4α,4aα,8aβ)-4-acetylamino-1-propylspiro[decahydroquinoline-6,2'-(1',3'-dioxolane)]

A solution was prepared of 1.1 g of rac-(4α,4aα,8aβ)-4-acetylamino-1-propylspiro[decahydroquinoline-6,2'-(1',3'-dioxolane)]in 20 ml of concentrated hydrochloric acid and 100 ml of water. The mixture was stirred at room temperature for 1 hour and then poured onto ice. The hydrogen ion concentration of the resulting mixture was adjusted to pH 11. The product was extracted into a solution of $CHCl_3$/i-PrOH (3:1), which was then evaporated to give 0.97 g of an off-white solid identified by rac-(4α,4aα,8aβ)-4-acetylamino-1-propyldecahydroquino- lin-6-one.

EXAMPLE 18 rac-(4aβ,8α,8aα)-8-Acetylamino-5-propyl-4,4a,5,6,7,8-,8a,9-octahydro-2H-pyrazolo[3,4-g]quinoline The title compound was prepared using the procedure of Example 12 and the compound of Preparation 11 as the starting material.

Mass spectrum: m/e=276.

| Analysis for dihydrate, Calcd: | C, 46.76; | H, 7.85; | N, 14.54 |
|---|---|---|---|
| Found: | C, 46.50; | H, 7.12: | N, 14.78 |

EXAMPLE 19 rac-(4aβ,8α,8aα)-5-Propyl-4,4a,5,6,7,8,8a,9-octahydro-2H-pyrazolo[3,4-g]quinolin-8-amine The title product was prepared by hydrolysis of the compound of Example 18.
Mass spectrum: m/e=235.
UV spectrum: ; $\lambda_{max}=221$; $\epsilon=5670$.
Infrared spectrum (KBr): 3270, 3245, 2900, 1680 $cm^{-1}$.

PREPARATION 12 rac-(4β,4aα,8aβ)-4-Acetylamino-1-propyldecahydroquinolin-6-one

The title product was prepared by acylating rac-(4β,4aα,8aβ)-1-propylspiro[decahydroquinoline-6,2'-(1',3,'-dioxolan)]-4-amine (Preparation 9), then hydrolyzing the resulting rac-(4β,4aα,8aβ)-4-acetyl- amino-1-propyl-spiro[decahydroquinoline-6,2'-(1',3'-dioxolane)] using the procedures of Preparation 11.

EXAMPLE 20 rac-(4aβ,8β,8aα)-8-Acetylamino-5-propyl-4,4a,5,6,7,8-,8a,9-octahydro-2H-pyrazolo[3,4-g]quinoline The title compound was prepared using the procedure of Example 12 and the compound of Preparation 12 as the starting material. The dihydrochloride salt was then formed and recrystallized from MeOH/EtOAC.
Mass spectrum: m/e=276.

| Analysis Calcd: | C, 51.58; | H, 7.50; | N, 16.04 |
|---|---|---|---|
| Found: | C, 51.32, | H, 7.38; | N, 15.81 |

EXAMPLE 21 rac-(4aβ,8β,8aα)-5-Propyl-4,4a,5,6,7,8,8a,9-octahydro-2H-pyrazolo[3,4-g]quinolin-8-amine The title product was prepared by acid hydrolysis of the compound of Example 20. The trihydrochloride salt was then formed and recrystallized from MeOH/EtOAC.
Mass spectrum: 235, 215, 149, 80.

EXAMPLE 22

7-(2-Amino-5-propyl-trans-4,4a,5,6,8a,9-hexahydrothiazolo-[4,5-g]quinoline)methanol The product of Example 3 (2.6 g, 8.1 mmole) was reduced using 5 equivalents of diisobutylaluminum hydride in methylene cloride to produce the title product (1.7 g).
Mass spectrum: m/e=323, 279.

EXAMPLE 23

7-(2-Methyl-5-propyl-trans-4,4a,5,6,8a,9-hexahydro-2H-pyrazolo[3,4-g]quinoline)methanol and
7-(1-Methyl-5-propyl-trans-4,4a,5,6,8a,9-hexahydro-1H-pyrazolo[3,4-g]quinoline)methanol A solution of 650 mg (5.8 mmole) of potassium tert-butoxide in 10 ml of THF was cooled to 0° C. To this was added a solution of 480 mg. (2.1 mmole) of 3-hydroxymethyl-1-propyl-trans-1,2,4a,5,6,7,8,8a-octahydroquinolin-6-one (Preparation 2), 600 mg (8.5 mmole) of ethyl formate, and 15 ml of THF. The mixture was warmed to room temperature and stirred for 5 hours, after which 2 ml of methyl hydrazine was added and the hydrogen ion concentration was adjusted to pH 9 while the mixture was cooled. The mixture was stirred overnight at room temperature and, then poured into water. The product was extracted into a solution of CHCl$_3$/i-PrOH (3:1), which was then evaporated to give 560 mg. of product, represented by two spots on TLC. The two isomers were separated on a silica gel column using 7% MeOH/CH$_2$Cl$_2$ containing a trace of NH$_4$OH. The fractions shown by TLC to contain 7-(2-methyl-5-propyl-trans-4,4a,5,6,8a,9-hexahydro-2H-pyrazolo[3,4-g]quinoline)methanol were combined, and the tosylate salt of this product was formed. This was recrystallized from MeOH/EtOAC, giving the tosylate salt of 7-(2-methyl-5-propyl-trans-4,4a,5,6,8a,9-hexahydro-2H-pyrazolo[3,4-g]quinoline)methanol as a yellow solid. M.P. 232°–233° C.

The fractions shown by TLC to contain 7-(1-methyl-5-propyl-trans-4,4a,5,6,8a,9-hexahydro-1H-pyrazolo[3,4-g]quinoline)methanol were combined, and the hydrochloride salt of this product was formed. This was recrystallized from MeOH/EtOAc to give the hydrochloride salt of 7-(1-methyl-5-propyl-trans-4,4a,5,6, 8a,9-hexahydro-1H-pyrazolo[3,4-g]quinoline)-methanol as a light yellow solid. M.P. 215°–216° C.

PREPARATION 13 rac-(3α,4aα,8aβ)-3-(1-Propylspiro[decahydroquinoline-6,2'-(1',3'-dioxolane)])methanol Ammonia (125 ml) was distilled through a BaO column, and 450 mg (65 mmole) of lithium was dissolved therein. To this solution 2.0 g (6.5 mmole) of ethyl 1'-propyl-trans-spiro[1,3-dioxolane-2,6'-(1',2',4a',5', 6',7',8',8a'-octahydroquinoline)]-3'-carboxylate (Preparation 1), 1.2 g (26 mmole) of ethanol, and 30 ml of THF were added slowly. The mixture was stirred for 30 minutes, and then ethanol was slowly added until the color faded. Nitrogen was blown over the mixture to evaporate the ammonia. The residue was taken up in water. The product was extracted from the aqueous mixture into methylene chloride, which was then dried using sodium sulfate, and evaporated to give 1.5 g of product. This was passed through a silica gel column with 3→5% MeOH/CH$_2$Cl$_2$ containing a trace of NH$_4$OH. The fractions shown by TLC to contain the title product were combined yielding 1.2 g thereof.

PREPARATION 14 rac-(3α,4aα,8aβ)-3-Hydroxymethyl-1-propyldecahydroquinoline-6-one

A solution of 1.2 g of rac-(3α,4aα,8aβ)-3-(1propyl-spiro[decahydroquinoline-6,2'-(1',3'-dioxolane)]methanol (Preparation 13) in 50 ml of water and 20 ml of concentrated hydrochloric acid was prepared and stirred for 1 hour. It was then poured into ice. The resulting mixture was made basic. Then the product was extracted into a solution of CHCl$_3$/i-PrOH (3:1), which was dried using sodium sulfate and evaporated to give 0.99 g of rac-(3α,4aα, 8aβ)-3-hydroxymethyl-1-propyldecahydro- quinoline-6-one.

EXAMPLE 24 rac-(4β,7α,8aα)-7-(5-Propyl-4,4a,5,6,7,8,8a,9-octahydro-2H-pyrazolo[3,4-g]quinoline)methanol To a solution of 0.47 g (2.1 mmole) of rac-(3α, 4aα,-8aβ)-3-hydroxymethyl-1-propyldecahydroquinoline-6-one (Preparation 14) in 50 ml of toluene there was added 1.4 ml (5.2 mmole) of tris(dimethylamino)methane. The mixture refluxed for 3 hours. The toluene was evaporated, and to a solution of this material in 50 ml of methanol was added 3 ml of hydrazine. The mixture was stirred at room temperature overnight, and was then poured into water. The product was extracted from the aqueous mixture into CHCl$_3$/i-PrOH (3:1). This was dried with sodium sulfate and evaporated giving an orange semi-solid product, which was passed through a silica gel column with 5→7% MeOH/CH$_2$Cl$_2$ containing a trace of NH$_4$OH. The fractions shown by TLC to contain the product were combined to give 300 mg of the title compound. This was converted to the hydrochloride salt, which was recrystallized from MeOH/EtOAc.

Analysis Calcd: C, 52.18; H, 7.82; N, 13.04
Found: C, 52.07; H, 7.92; N, 13.07

EXAMPLE 25 rac-(5aβ,8α,9aα-8-2-amino-5,5a,6,7,8,9,9a,10-octahydropyrido[2,3-gquinazoline)methanol To a solution of 0.5 g (2.2 mmole) of rac-(3α,4aα,-8aβ)-3-hydroxymethyl-1-propyldecahydroquinoline6-one (Preparation 14) in 50 ml of toluene there was added 1.5 ml (5.6 mmole) of tris(dimethylamino)methane. The mixture refluxed for 2 hours. The toluene was evaporated, and to a solution of the residue in 75 ml of ethanol was added a suspension of 130 mg (2.2 mmole) of guanidine in 50 ml of ethanol. The mixture was heated to reflux for 1 hour, stirred at room temperature overnight, and was then poured into water. The product was extracted from the aqueous mixture into CHCl$_3$/i-PrOH (3:1) which was then dried using sodium sulfate and evaporated, giving 590 mg of a yellow solid. This was passed through a silica gel column with 7% MeOH/CH$_2$Cl$_2$ containing a trace of NH$_4$OH. The fractions shown by TLC to contain the product were combined and recrystallized from MeOH/EtOAc, yielding 215 mg.

Mass spectrum: 276, 247, 204, 168, 154, 146, 136, 126.
Proton nmr (360 MHz) DMSOds: 7.98 (s,1H), 6.21 (s,2H), 0.82 (t,3H).

PREPARATION 15 rac-(3α,4aα,8aβ)-3-Methoxymethyl-1-propyldecahydrquinoline-6-one

The title product was prepared using the procedures of Preparation 4 and the product of Preparation 13 as the starting material.

EXAMPLE 26 rac-(4aβ,7α,8aα)-7-Methoxymethyl-5-propyl-4,4a,5,6,7,8,-8a,9-octahydro-2H-pyrazolo[3,4-g]quinoline The title product was prepared using the procedure of Example 24 and rac-(3α,4aα,8aβ)-3-methylthiomethyl-1-propyldecahydroquinoline-6-one (Preparation 15) as the starting material. This was converted to the dihydrochloride salt and recrystallized with MeOH/CH$_2$Cl$_2$ to give a tan solid.

Mass spectrum: 263, 248, 234, 169, 154, 140, 119, 71.

Analysis Calcd: C, 53.57; H, 8.09; N, 12.49
Found: C, 53.53; H, 7.90; N, 12.42

EXAMPLE 27 rac-(5a$\beta$,8$\alpha$,9a$\alpha$)-8-methoxymethyl-6-propyl-5,5a,6,7,8,9,9a,10-octahydropyrido[2,3-g]quinazoline-2-amine The title product was prepared using the procedure of Example 25 and rac-(3$\alpha$,4a$\alpha$,8a$\beta$)-3-methoxy- methyl-1-propyldecahydroquinoline-6-one (Preparation 15) as the starting material. This was recrystallized from MeOH/EtOAc.

Mass spectrum: 290, 275, 261, 245, 218, 179, 168, 154, 136, 122, 71.

Analysis Calcd: C, 66.17; H, 9.09; N, 19.29
Found: C, 66.41; H, 9.25; N, 19.39

PREPARATION 16 rac-(3$\alpha$,4a$\alpha$,8a$\beta$)-3-Methylthiomethyl-1-propyldecahydroquinolin-6-one

A. Conversion of rac-(3$\alpha$,4a$\alpha$,8a$\beta$)-3-(1-propylspiro[decahydroquinoline-6,2'-(1',3'-dioxolane)])methanol (Preparation 13) to corresponding methanesulfonat A solution of 1g (3.7 mmole) of rac-(3$\alpha$,4a$\alpha$,8a$\beta$)-3-(1-propylspiro[decahydroquinoline-6,2'-(1',3'-dioxolane)]-)methanol in 25 ml of pyridine was cooled to 0° C. To this 0.55 g (4.8 mmole) of methanesulfonyl chloride was added, and the mixture was stirred at room temperature for 2 hours. The mixture was then poured into water, and the hydrogen ion concentration was adjusted to pH 10. The product was extracted into methylene chloride, which was then dried to give rac-(3$\alpha$,4a$\alpha$,8a$\beta$)-3-methylsulfonyloxymethyl-1-propylspiro[decahydroquinolin6,2'-(1',3'dioxolane)] as a brown oil.

B. Substitution of methyl mercaptide for methylsulfonyloxy in rac-(3$\alpha$,4a$\alpha$,8a$\beta$)-3-methylsulfonyloxymethyl-1-propylspiro[decahydroquinolin-6,2'-(1',3'dioxolane)].

After rinsing 355 mg (7.4 mmole) of sodium hydride (55% in mineral oil) with hexane, it was suspended in 25 ml of DMF and 10.6 ml (37mmole) of a 3.5M solution of methanethiol was added. An additional 4 ml (14 mmole) of the methanethiol was added, whereupon the solution turned a clear light amber. This was cooled to 0° C. and the rac-(3$\alpha$,4a$\alpha$,8a$\beta$)-3-methylsulfonyloxymethyl-1-propylspiro[decahydroquinolin-6,2'-(1',3'dioxolane)](3.7 mmole) produced in Step A in 10 ml of DMF was slowly added. The mixture was allowed to come to room temperature and was stirred overnight. The mixture was then poured into water. The product was extracted into CHCl$_3$/i-PrOH (3:1), which was then dried using sodium 2 sulfate and evaporated to give 960 mg of rac-(3$\alpha$,4a$\alpha$,8a$\beta$)-3-methylthiomethyl-1-propylspiro[decahydroquinoline-6,2'-(1',3'-dioxolane)] as a brown oil.

Mass Spectrum: 299, 284, 270, 252, 198, 101.

Hydrolysis of rac-(3$\alpha$,4a$\alpha$,8a$\beta$)-3-methythiomethyl-1-propylspiro[-decahydroquinoline-6,2'-(1',3'-dioxolane)

A solution of 1.35 g of rac-(3$\alpha$,4a$\alpha$,8a$\beta$)-3methylthiomethyl-1-propylspiro[decahydroquinoline-6,2'-(1',3'-dioxolane) in 50 ml of water and 20 ml of concentrated hydrochloric acid was prepared and stirred for 1 hour. It was then poured into ice. The resulting mixture was made basic. Then the product was extracted into a solution of CHCl$_3$/i-PrOH (3:1), which was dried using sodium sulfate and evaporated to give 1.1 g of product. This was passed through a silica gel column with hexane/THF (5:1) containing a trace of NH$_4$OH. The fractions shown by TLC to contain rac-(3$\alpha$,4a$\alpha$,8a$\beta$)-3-methylthiomethyl-1-propyldecahydroquinolin-6-one were combined. Yield 900 mg.

EXAMPLE 28 rac-(4$\beta$,7$\alpha$,8a$\alpha$)-7-Methylthiomethyl-1-propyl-4,4a,5,6,7,8,8a,9-octahydro-2H-pyrazolo[3,4-g]quinoline The title product was prepared using the process of Example 24 and the product of Preparation 16 as the starting material. The dihydrochloride salt was then prepared and recrystallized from MeOH/EtOAC.

Mass Spectrum: 279, 264, 250, 232, 185, 170, 119, 87.

EXAMPLE 29 rac-(5$\beta$,8$\alpha$,9a$\alpha$)-8-Methylthiomethyl-6-propyl-5,5a,6,7,8,9,9a,10-octahydropyrido-[2,3-g]quinazolin-2-amine The title compound was prepared using the process of Example 25 and the product of Preparation 16 as the starting material.

Analysis, calculated: C, 62.71; H, 8.55; N, 18.28
Found: C, 62.90; H, 8.73; N, 18.38

Mass Spectrum: 306, 292, 277, 259, 245 198, 184, 170, 146, 122.

PREPARATION 17 rac-(3$\alpha$,4a$\alpha$,8a$\beta$)-Ethyl 1-propylspiro[decahydroquinoline-6,2'-(1',3'-dioxolane)-3-carboxylate To a solution of 4.5g (14.5 mmole) of rac-(3$\beta$,4a$\alpha$,8a$\beta$)-ethyl 1-propylspiro[decahydroquinoline-6,2'-(1',3'-dioxolane)-3-carboxylate (Preparation 19) in 75 ml of THF at −78° C. was added 72.3 ml (72.3 mmole) of a 1.0M solution of lithium diisopropylamide. The mixture was stirred at 0° C. for 2½ hours, then cooled to −78° C., and 20 ml of acetic acid in 50 ml of THF at −78° C. was added. The mixture was allowed to come to room temperature, and a gel formed. This was poured into water. The hydrogen ion concentration was adjusted to pH 11. The product was extracted into CH$_2$Cl$_2$, which was then dried using sodium sulfate and evaporated to give 4.6 g of product. The isomers were separated on a silica gel column using hexane/EtOAC (3:1). The fractions shown by TLC to contain the (3$\alpha$,4a$\alpha$,8a$\beta$) racemate were combined to give 2.0 g of an oil. The fractions shown by TLC to contain the (3β,4aα,8aβ) racemate were combined to give 1.0 g of product.

PREPARATION 18 rac-(3α,4aα, 8aβ)-Ethyl 6-oxo-1-propyldecahydroquinoline-3-carboxylate

The title compound was prepared by acid hydrolysis of 2.0 g of rac-(3α,4aα,8aβ)-ethyl 1-propyl-spiro[-decahydroquinoline-6,2'-(1',3'-dioxolane)-3-carboxylate (Preparation 17) in 150 ml of water containing 30 ml of concentrated hydrochloric acid at room temperature.

EXAMPLE 30 rac-(4β, 7α, 8aα)-Ethyl 2-amino-5-propyl-4,4a,5,6,7,8,8a,9-octahydrothiazolo[4,5-g]quinoline-7-carboxylate The title compound was prepared using the general procedure of Example 3 and the product of Preparation 18 as the starting material.
Mass Spectrum: m/e=323.

EXAMPLE 31 rac-(4β, 7α,8aα)-7-(2-Amino-5-propyl-4,4a,5,6,7,8,8a-octahydrothiazolo[4,5-g]quinoline)methanol The title product was prepared by reducing 560 mg (1.8 mmole) of rac-(4β,7α,8aα)-ethyl 2-amino-5-propyl-4,4a,5,6,7,8,8a,9-octahydrothiazolo[4,5-g]-quinoline-7-carboxylate (Example 30) with 8.8 ml of a 1M solution of diisobutylaluminum hydride (8.8 mmole) in 100 ml of THF. Yield: 350 mg.
Mass Spectrum: m/e=281.

EXAMPLE 32 rac-(4β,7α,8aβ)-7-(5-propyl-4,4a,5,6,7,8,8a-octahydrothiazolo[4,5-g]quinoline)methanol A solution of 360 mg (1.2 mmole) of rac-(4aβ,7α,-8aβ)-7-(2-amino-5-propyl-4,4a,5,6,7,8,8a-octahydrothiazolo[4,5-g]quinoline)methanol (Example 31) in 30 ml of 85% phosphoric acid was cooled to 0°. Then 90 mg (1.5 mmole) of sodium nitrite dissolved in as small an amount of water as possible was slowly added under the surface of the reaction mixture. The resulting mixture was added dropwise to 30 ml of 50% hypophosphorous acid ($H_3PO_2$) at 0° C. The mixture was stirred at room temperature until gas evolution ceased. This took about 1 hour. The mixture was poured onto ice, and the hydrogen ion concentration of the mixture was adjusted to pH 11. Water was added to dissolve the precipitate that formed; then the product was extracted into a solution of $CHCl_3$/i-PrOH (3:1). This solution was dried using sodium sulfate and evaporated to give 280 mg of the title product. This was passed through a silica gel column with 5% MeOH/$CH_2Cl_2$ containing a trace of $NH_4OH$. The appropriate fractions were combined, and the dihydrobromide salt of the product was formed and recrystallized from MeOH/EtOAC.

Analysis, calculated: C, 39.27; H, 5.65; N, 6.54
found: C, 39.01; H, 5.62; N, 6.78

Preparations 19–24 and Examples 33–40 relate to the β racemates defined in formula (3) and to intermediates used in preparation thereof.

PREPARATION 19 rac-(3β,4aα,8aβ)-Ethyl 1-propylspiro[decahydroquinoline-6,2'-(1',3'-dioxolane)]-3-carboxylate A 5 g sample of ethyl 1'-propyl-trans-spiro-[1,3-dioxolane-2,6'-(1',2',4a',5',6',7',8',8a'-octahydroquinoline)]-3-carboxylate (Preparation 1) was hydrogenated at room temperature in 200 ml of 2B ethanol using about 5 g of Raney ® nickel with $H_2$ at 50 psi for 2½ hours to give 4.49 g of the title product.

PREPARATION 20 rac-(3β,4aα,8aβ)-3-(1-Propylspirodecahydroquinoline-6,2'-(1',3'-dioxolane)])methanol A solution of 2.6 g (67.5 mmole) of lithium aluminum hydride in 400 ml of THF was prepared. To this a solution of 17.5 g (56.3 mmole) of rac-(3β,4aα,8aβ)ethyl 1-propylspiro[decahydroquinoline-6,2'-(1',3'-dioxolane)]-3-carboxylate (Preparation 19) in 350 ml of THF was slowly added. Then the following additions were made sequentially: 2.5 ml of water, 2.5 ml of 15% NaOH, 7.5 ml of water. The mixture was then filtered through a pad of celite and the filtrate was evaporated, producing an oil. A glutanous precipitate formed. The oil was dissolved in $CH_2Cl_2$, which was then dried using sodium sulfate, filtered, and evaporated, giving 15.4 of rac-(3β, 4aα,8aβ)-3-(1-propylspiro[decahydroquinoline-6,2'-(1',3'-dioxolane)])methanol.

PREPARATION 21 rac-(3β,4aα,8aβ)-3-Hydroxymethyl-1-propyldecahydroquinolin-6-one

The title product was prepared by hydrolyzing a 2.0 g sample of rac-(3β,4aα,8aβ)-3-(1-propylspiro[decahydroquinoline-6,2'-(1',3'-dioxolane)])methanol (Preparation 20) in a solution of 100 ml of water and 40 ml of concentrated HCl at room temperature.

EXAMPLE 33 rac-(5aβ,8β,9aα)-8-(2-amino-6-propyl-5,5a,6,7,8,9-,9a,10-octahydropyrido[2,3-g]quinazoline)methanol The title compound was made using the procedure of Example 25 and the product of Preparation 21 as the starting material. The dihydrochloride salt was then made and recrystalized from MeOH/EtOAC.
Mass Spectrum: 276, 247, 204, 168, 154, 146, 136, 126

Analysis, calc: C, 51.58; H, 7.50; N, 16.04; O, 20.30
found: C, 51.81; H, 7.79; N, 15.91; O, 20.17

PREPARATION 22 rac-(3β,4aα,8aβ)-3-Methoxymethyl-1-propyldecahydroquinolin-6-one

The title product was prepared using the procedures of Preparation 4 and the product of Preparation 20 as the starting material.

EXAMPLE 34 rac-(5aβ,8β,9aα)-8-Methoxymethyl-6-propyl-5,5a,6,7,8,9.9a,10-octahydropyrido[2,3-g]quinazolin-2-amine The title product was prepared using the, procedure of Example 25 rac-(3β,4aβ,8aβ)-3-methoxymethyl-1-propyldecahydroquinolin-6-one (Preparation 22) as the starting material.

Analysis calcd: C, 66.17; H, 9.02; N, 19.29
found: C, 65.89; H, 8.89; N, 19.16

PREPARATION 23 rac-(3β,4aα,8aβ)-3-Methylthiomethyl-1-propyldecahydroquinolin-6-one

The title product was prepared from rac-(3β,4aα,8aβ)-3-(1-propylspiro[decahydroquinoline-6,2'-(1',3'-dioxolane)])methanol (Preparation 20) using the process of Preparation 16. In Step B (substitution of methyl mercaptide for methylsulfonyloxy) it was necessary to heat the reaction to 70° C. for two hours after the mixture was stirred overnight at room temperature.

EXAMPLE 35 rac-(5aβ,8β,9aβ)-8-Methylthiomethyl-1-propyl-5,5a,6,7,8,9,9a,10-octahydropyrido[2,3-g]quinazolin-2-amine The title compound was prepared from the product of Preparation 23 using the process of Example 25.
Mass spectrum: 306, 292, 277, 259, 245, 188, 146.
The monohydrochloride salt was formed and recrystallized from MeOH/EtOAC. M.P.>250° C.

Analysis Calcd: C, 56.04; H, 7.94; N, 16.34
Found: C, 56.16; H, 7.73; N, 16.09

PREPARATION 24 rac-(3β,4aα,8aβ)-Ethyl 6-oxo-1-propyldecahydroquinoline-3-carboxylate

The title compound was prepared by hydrolyzing 1.0 g of rac-(3β,4aα,8aβ)-ethyl 1-propylspiro[decahydroquinoline-6,2'-(1',3'-dioxolane)]-3-carboxylate (Preparation 19) in a solution of 100 ml of H₂O and 20 ml of concentrated HCl at room temperature.

EXAMPLE 36 rac-(4β,7β,8aα)-Ethyl 2-amino-5-propyl-4,4a,5,6,7,8,8a,9-octahydrothiazolo4,5-g]quinoline-7-carboxylate The title compound was prepared from rac-(3β,4aα,8aβ)-ethyl 6-oxo-1-propyldecahydroquinoline-3-carboxylate (Preparation 24) using the general process as EXAMPLE 3.
Mass spectrum: m/e=323.

EXAMPLE 37 rac-(4aβ,7β,8aβ)-7-(2-Amino-5-propyl-4,4a,5,6,7,8,8a-octahydrothiazolo[4,5-g]quinoline)methanol The title compound was prepared by reducing 520 mg (1.6 mmole) of rac-(4aβ,7β,8aβ)-ethyl 2-amino-5-propyl-4,4a,5,6,7,8,8a,9-octahydrothiazolo[4,5-g]quino line-7-carboxylate (Example 36) with 8.0 ml of 1M solution of diisobutylaluminum hydride (in CH₂Cl₂) in 75 ml of THF.
Mass spectrum: m/e=281.
I.R.: 3297, 3103, 2918, 1760, 1541 cm⁻.

EXAMPLE 38 rac-(4aβ,7β,8aβ)-7-(5-propyl-4,4a,5,6,7,8,8a-octahydrothiazolo[4,5-g]quinoline)methanol The title compound was prepared from rac-(4aβ,7β,8aβ)-7-(2-Amino-5-propyl-4,4a,5,6,7,8,8a-octahydrothiazolo[4,5-g]quinoline)methanol (Example 37) using the procedure of Example 32. The dihydrobromide salt was formed and recrystallized from MeOH/EtOAC.
Mass spectrum: m/e=266.
I.R.: 3405, 1650 cm⁻.

PREPARATION 25

Ethyl 8-[(phenylmethyl)amino]-1,4-dioxaspiro[4.5]dec-7-ene-7-carboxylate

Ethyl 8-oxo-1,4-dioxaspiro[4.5]decane-7carboxylate (352.8 g, 1.6 mole) was dissolved in ethyl alcohol (1500 ml), and benzylamine (365 g, 3.6 mole) was added. The mixture was stirred, heated to about 50° C. for about 2 hours, and then another equivalent of benzylamine (171 g, 1.6 mole) was added. The mixture was then poured into water. The product was extracted with methylene chloride, dried with sodium sulfate and evaporated to give an oil. Excess benzylamine was vacuum distilled off at 0.1 mm Hg and 60-65° C. allowing the pot residue, which contained the product, to reach 110° C. This was then diluted with methanol (1:1 by volume). The resulting, mixture was allowed to cool Crystals formed and 395.4 g of white crystals were isolated by filtration.

A second crop of 75.6 g of tan crystals was isolated from the mother liquor, giving a total of 471.0 g of the title compound.

PREPARATION 26

Ethyl 8-[(phenylmethyl)amino]-1,4-dioxaspiro[4.5]decane-7-carboxylate

Ethyl 8-[(phenylmethyl)amino]-1,4-dioxaspiro-[4.5]-dec-7-ene-7-carboxylate (395.4 g, 1.3 mole) and acetic acid (75.0 ml, 1.3 mole) were added to ethanol (4 l). Sodium cyanoborohydride (82.0 g, 1.3 mole) was added in portions over 3 hours. The mixture was stirred overnight, then poured into water. The pH was adjusted to 10, and the product was extracted with methylene chloride, which was then dried with sodium sulfate and evaporated to give a yellow oil having small clear lumps in it. This was dissolved in THF and poured through 3 inches of basic alumina, which was then rinsed well with THF. The filtrate was evaporated to give 397.2 g (99.9%) of the title product as a yellow-green oil.

PREPARATION 27

Ethyl 8-amino-1,4-dioxaspiro[4.5]decane-7-carboxylate

Ethyl 8-[(phenylmethyl)amino]-1,4-dioxaspiro[4.5]-decane-7-carboxylate (397.2 g, 1.3 mole) was combined with 2563 ml of ethanol and 80 g of 5% palladium on activated carbon and hydrogenated at 50 p.s.i. for 6 hours at 45°-50° C. The catalyst was separated by filtration, and the filtrate was evaporated. When taken up in methylene chloride a semi-solid precipitated and was filtered out. The filtrate was evaporated to yield 277.7 g (97.4%) of the title product.

PREPARATION 28

Ethyl 8-amino-trans-1,4-dioxaspiro[4.5]decane-7-carboxylate

Sodium metal (27.7 g, 1.2 mole) was reacted with ethanol (1 l), then ethyl-8-amino-1,4-dioxaspiro[4.5]-decane-7-carboxylate (137.7 g, 0.6 mole) in ethanol (400 ml) was added. The mixture was refluxed for 1½ hours, then cooled to room temperature, poured into ice, and made basic. The product was extracted with methylene chloride, dried with sodium sulfate and evaporated to give 118.0 g (85.7%) of the title product.

PREPARATION 29

Ethyl 8-(propylamino)-trans-1,4-dioxaspiro[4.5]-decane-7-carboxylate

Ethyl 8-amino-trans-1,4-dioxaspiro[4.5]decane-7-carboxylate (118.0 g, 0.52 mole) was dissolved in DMF (1 l) and potassium carbonate (107 g, 0.77 mole) and propyl bromide (158.4 g, 1.3 mole) were added. The mixture was heated to 50° C. for three hours, then poured into water, and the hydrogen ion concentration was adjusted to pH 10. The product was extracted with methylene chloride, dried and evaporated to give 136 g of a dark orange oil.

PREPARATION 30

Ethyl 8-[(3-ethoxy-3-oxopropyl)propylamino]-trans-1,4-dioxaspiro[4.5]decane-7-carboxylate Ethyl 8-(propylamino)-trans-1,4-dioxaspiro[4.5]-decane-7-carboxylate (129.6 g, 0.48 mole) was dissolved in ethanol (1500 ml), then ethyl acrylate (479 g, 4.8 mole) was added. The mixture was refluxed overnight, then additional ethyl acrylate (479 g, 4.8 mole) was added. The mixture was refluxed for 24 hours, at which time a third addition of ethyl acrylate (479 g, 0.48 mole) was made, followed by 60 hours of reflux. The mixture was then cooled to room temperature, poured into water, and the hydrogen ion concentration was adjusted to pH 10. The product was extracted with methylene chloride, dried with sodium sulfate and evaporated to give 177.4 g of crude product. This was purified by HPLC to give 102.1 g of the title product (59.8%).

EXAMPLE 39

Ethyl 4-oxo-1-propyl-trans-spiro[decahydroquinoline-6,2'-(1',3'-dioxolane)]-3-carboxylate THF (500 ml) was added to potassium t-butoxide (61.6 g, 0.55 mole), and to this mixture ethyl 8-[(3-ethoxy-3-oxapropyl)propylamino]-1,4-dioxaspiro[4.5]-decane-7-carboxylate (98.0 g, 0.27 mole) dissolved in 500 ml of THF was slowly added. The mixture was then poured onto ice and the hydrogen ion concentration was adjusted to pH 10. The product was extracted with methylene chloride, dried with sodium sulfate, and evaporated to yield 87.2 g (97.7%) of the title product.

The compounds of this invention are useful as prolactin inhibitors and as such they can be employed in the treatment of inappropriate lactation such as postpartum lactation and galactorrhea. As evidence of their utility in the treatment of conditions in which it is desirable to reduce the prolactin level, the compounds of this invention have been shown to inhibit prolactin according to the following procedure.

Adult male rats of the Sprague-Dawley strain weighing about 200 g were housed in an air-conditioned room with controlled lighting (lights on 6 a.m.-8 p.m.) and fed lab chow and water ad libitum. In the testing of the reserpinized male rat at 50 μg/kg of compound under test, each rat received an intraperitoneal injection of 2.0 mg. of reserpine in aqueous suspension 18 hours before administration of the test drug. The purpose of the reserpine was to keep prolactin levels uniformly elevated. In the testing of the nonreserpinized male rat at 1000 μg/Kg of compound under test, the preceding procedure was omitted. The compounds under test were dissolved in 10 percent ethanol, and were injected intraperitoneally. Each compound was administered at each dose level to a group of 10 rats, and a control group of 10 intact males received an equivalent amount of 10 percent ethanol. One hour after treatment, all rats were killed by decapitation, and 150 μl aliquots of serum were assayed for prolactin.

The difference between the prolactin level of the treated rats and prolactin level of the control rats, divided by the prolactin level of the control rats gives a number that, when multiplied by 100, is the percent inhibition of prolactin secretion attributable to the compounds of this invention. These inhibition percentages are given in Table 1.

Dopamine agonists have been found to affect turning behavior in 6-hydroxydopamine-lesioned rats in a test procedure designed to uncover compounds useful for the treatment of Parkinsonism. In this test, nigro-neostriatal-lesioned rats are employed, as prepared by the procedure of Ungerstedt and Arbuthnott, *Brain Res*, 24, 485 (1970). A compound having dopamine agonist activity and the ability to pass through the blood brain barrier into the striatum of the brain causes the rats to turn in circles contralateral to the side of the lesion. After a latency period, which varies from compound to compound, the number of turns is counted over a 15-minute period.

Results obtained from such testing are set forth for representative compounds in Table 1. In the table, column 1 identifies the compound by example number; columns 2 and 3, the percent prolactin inhibition at 50 μg/Kg for reserpinized male rats and 1000 μg/Kg for nonreserpinized male rats; and column 4, the percent of test animals exhibiting turning behavior.

TABLE 1

| Compound (Ex. No.) | Percent Prolactin Inhibition | | % of Rats Exhibiting Turning Behavior |
|---|---|---|---|
| | 50 μg/Kg[a] | 1000 μg/Kg[b] | 1.0 mg/Kg |
| 1 | 71 | — | 0 |
| 2 | 76 | — | 82 |
| 6 | — | 90 | — |
| 8 | — | 84 | 80 |
| 11 | — | 84 | 33 |
| 13 | 14 | 94 | 0 |
| 14 | 62 | — | 0 |
| 15 | 83 | — | 100 |
| 16 | 27 | — | — |
| 22 | 88 | — | — |
| 23(1H) | — | 83 | — |
| 23(2H) | — | 84 | — |
| 24 | 3 | 70 | — |
| 25 | — | 87 | — |
| 26 | — | 89 | — |
| 27 | — | 89 | — |

TABLE 1-continued

| Compound (Ex. No.) | Percent Prolactin Inhibition | | % of Rats Exhibiting Turning Behavior |
|---|---|---|---|
| | 50 μg/Kg[a] | 1000 μg/Kg[b] | 1.0 mg/Kg |
| 28 | — | 85 | — |
| 34 | — | 92 | — |
| 35 | — | 95 | — |

[a]Percent reduction from controls in serum prolactin levels following a dose of 50 μg/Kg in the reserpinized male rat.
[b]Percent reduction from controls in serum prolactin levels following a dose of 1000 μg/Kg in the nonreserpinized male rat.

Dopamine agonists which pass through the blood-brain barrier and enter the brain have been shown to decrease brain levels of dopamine metabolites such as 3,4-dihydroxy phenylacetic acid (DOPAC) and homovanillic acid (HVA). Tests described by Perry and Fuller, *Soc. Neurosci. Abstr.*, 5, 348 (1979) evaluate the effect compounds have on dopamine metabolite levels in the brain. Compounds of this invention were subjected to these testing procedures and the results of representative compounds are given in Table 2.

Dopamine agonists that enter the brain give rise to elevated serum corticosterone levels. Compounds of this invention were subjected to the testing procedure of Solem and Brink-Johnsen, *Scand. J. Clin. Lab. Invest.* (Suppl. 80) 17:1 (1965) to determine their effects on serum corticosterone levels. Results of representative compounds are given in Table 2 below. In the table, column 1 identifies the compound by example number; column 2 and 3, minimum effective dose to alter brain dopamine metabolite levels; and column 4, minimum effective dose causing serum corticosterone elevation.

TABLE 2

| Compound (Ex. No.) | Minimum Effective Dose, μg/Kg, i.p. | | |
|---|---|---|---|
| | Brain Dopamine Metabolites | | Serum Corticosterone Elevation |
| | DOPAC[a] | HVA[b] | |
| 1 | >3000 | 1000 | >3000 |
| 2 | 300 | 300 | 300 |
| 6 | 30 | 30 | 30 |
| 8 | 100 | 100 | 100 |
| 14 | >3000 | >3000 | >3000 |
| 22 | 100 | 30 | 1000 |
| 25 | 300 | 300 | 1000 |
| 26 | >3000 | 30 | 30 |
| 27 | 30 | 30 | 30 |
| 28 | 1000 | 100 | 100 |
| 35 | 10 | 10 | 100 |

[a]DOPAC = 3,4-dihydroxyphenylacetic acid
[b]HVA = homovanillic acid

Compounds of Examples 1 and 14 are peripherally selective dopamine agonists. They are active in the inhibition of serum prolactin secretion by activation of dopamine receptors on the pituitary, a tissue which is not protected by the blood-brain barrier. These compounds do not elicit turning in the 6-hydroxydopamine-lesioned rat or cause changes in the levels of dopamine metabolites or serum corticosterone, which are activities mediated in brain regions protected by the blood-brain barrier. These compounds wold have utility to inhibit prolactin secretion without causing central dopaminergic side effects.

The compounds of this invention reduce the blood pressure of spontaneously hypertensive rats, as shown by the following experiment:

Adult male spontaneously hypertensive rats (SHR) (Taconic Farms, Germantown, N.Y.) weighing approximately 300 g were anesthetized with pentobarbital sodium (60 mg/kg, i.p.). The trachea was cannulated and the SHR respired room air. Pulsatile arterial blood pressure was measured from a cannulated carotid artery using a Statham transducer (P23 ID). Mean arterial blood pressure was calculated as diastolic blood pressure plus ⅓ pulse pressure. Drug solutions were administered i.v. through a catheter placed in a femoral vein. Arterial blood pressure was recorded on a multichannel oscillograph (Beckman, Model R511A). Fifteen minutes were allowed to elapse following surgery for equilibration of the preparation.

Table 3, which follows, gives the results of this test for representative compounds of this invention. In Table 3, column 1 identifies the compound by example number; and columns 2, 3, 4, 5, 6 and 7, the percent change in blood pressure at 0.1 μg/kg, 1 μg/kg, 10 μg/kg, 100 μg/kg, 1000 μg/kg and 10,000 μg/kg, respectively.

TABLE 3

% Change in Mean Arterial Blood Pressure in Anesthetized Spontaneously Hypertensive Rats

| Compound (Ex. No.) | 0.1 μg/kg | 1 μg/kg | 10 μg/kg | 100 μg/kg | 1000 μg/kg | 10000 μg/kg |
|---|---|---|---|---|---|---|
| 5 | −5.7 ± 0.3 | −24.2 ± 1.6 | −36.8 ± 6.2 | −43.0 ± 3.7 | −48.3 ± 2.8 | — |
| 6 | −1.4 ± 3.6 | −15.2 ± 3.7 | −35.6 ± 5.2 | 8.0 ± 2.7 | — | — |
| 8 | — | −18.0 ± 2.2 | −25.3 ± 2.2 | −30.6 ± 1.7 | −17.2 ± 3.5 | — |
| 11 | — | −11.0 ± 4.0 | −18.0 ± 6.6 | −26.7 ± 7.2 | −4.3 ± 4.2 | — |
| 12 | — | +2.8 ± 0.8 | +3.2 ± 0.6 | −1.6 ± 3.1 | −8.9 ± 1.5 | −37.8 ± 2.1 |
| 13 | — | −8.6 ± 0.8 | −8.4 ± 1.1 | −14.9 ± 0.7 | −14.6 ± 2.8 | — |
| 16 | — | +3.6 ± 0.3 | +3.2 ± 0.6 | −10.9 ± 1.1 | −28.6 ± 3.8 | — |
| 19 | — | +4.0 ± 1.5 | +1.5 ± 1.0 | −8.8 ± 1.4 | −13.3 ± 1.0 | — |
| 22 | −5.8 ± 1.4 | −19.0 ± 1.3 | −20.0 ± 1.6 | −44.2 ± 2.0 | −48.6 ± 0.8 | — |
| 24 | — | −4.2 ± 1.6 | −8.4 ± 0.6 | −18.4 ± 2.8 | −18.1 ± 0.9 | — |
| 26 | — | −10.8 ± 2.0 | −19.4 ± 1.6 | −27.6 ± 2.0 | −44.1 ± 3.4 | — |
| 32 | — | −8.4 ± 1.2 | −18.1 ± 1.0 | −37.1 ± 1.0 | −40.4 ± 3.9 | — |
| 34 | — | −20.2 ± 2.1 | −39.2 ± 3.5 | −27.2 ± 5.4 | −13.5 ± 2.3 | — |
| 35 | −18.9 ± 1.8 | −25.1 ± 2.2 | −33.6 ± 2.4 | −12.2 ± 1.5 | — | — |
| 38 | +5.2 ± 2.2 | −9.8 ± 2.0 | −20.6 ± 2.2 | −27.1 ± 6.2 | −37.0 ± 1.3 | — |

The compounds of this invention are administered for therapeutic purposes in a variety of formulations as illustrated below.

Hard gelatin capsules are prepared using the following ingredients:

|  | Quantity (mg./capsule) |
| --- | --- |
| Active compound | .1–2 mg |
| Starch dried | 200 |
| Magnesium stearate | 10 |

The above ingredients are mixed and filled into hard gelatin capsules.

A tablet formulation is prepared using the ingredients below:

|  | Quantity (mg./tablet) |
| --- | --- |
| Active compound | .1–2 mg |
| Cellulose, microcrystalline | 400 |
| Silicon dioxide, fumed | 10 |
| Stearic acid | 5 |

The components are blended and compressed to form tablets.

Alternatively, tablets each containing 0.1–2 mg. of active ingredient are made up as follows:

| Active ingredient | .1–2 mg. |
| --- | --- |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets.

Capsules each containing 0.1–2 mg. of medicament are made as follows:

| Active ingredient | .1–2 mg. |
| --- | --- |
| Starch | 59 mg. |
| Microcrystalline cellulose | 59 mg. |
| Magnesium stearate | 2 mg. |

The active ingredient, cellulose, starch and magnesium stearate are blended, passed through a No. 45 mesh U.S. sieve, and filled into hard gelatin capsules.

Suspensions each containing 0.1–2 mg. of medicament per 5 ml. dose are made as follows:

| Active ingredient | .1–2 mg. |
| --- | --- |
| Sodium carboxymethyl cellulose | 50 mg. |
| Syrup | 1.25 ml. |
| Benzoic acid solution | 0.10 ml. |
| Flavor | q.v. |

| -continued | |
| --- | --- |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

For oral administration, tablets, capsules or suspensions containing from about 0.1 to about 2 mg. of active drug per dose are given 3–4 times a day, giving a daily dosage of 0.3 to 8 mgs. or, for a 75 kg person, about 4.0 to about 107 mcg/kg. The intravenous dose is in the range from about 0.1 to about 100 mcg./kg.

We claim:

1. A BCD tricyclic ergoline part-structure analogue of the formula (1)

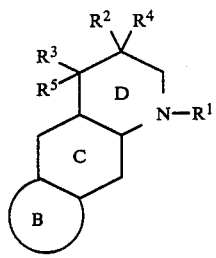

wherein:
the C and D rings are trans fused;
$R^1$ is $(C_1-C_3)$ alkyl, allyl, or cyclopropylmethyl;
$R^2$ is hydrogen, $CH_2OH$, $CH_2OCH_3$, $CH_2SCH_3$, $CH_2SOCH_3$, $CH_2SO_2CH_3$, $C_2OR^6$, or $CONR^7R^8$, where $R^6$ is hydrogen, $(C_1-C_4)$ alkyl or benzyl, and $R^7$ and $R^8$ are independently selected from hydrogen, $(C_1-C_4)$ alkyl, phenyl, benzyl, and phenethyl;
$R^3$ is hydrogen, OH, $NH_2$, $NHCOR^9$ or $NHSO_2NR^9R^{10}$, where $R^9$ and $R^{10}$ are independently selected from hydrogen, $(C_1-C_4)$ alkyl, and phenyl, or $R^3$ and $R^5$ combine to form =O or =NOH;
$R^4$ and $R^5$ are both hydrogen, or combine to form a carbon-carbon bond, except that $R^4$ is hydrogen when $R^5$ combines with $R^3$ to form =O or =NOH;
provided that one of $R^2$ and $R^3$ is hydrogen and the other is not hydrogen, and further provided that $R^2$ is hydrogen unless $R^4$ and $R^5$ combine to form a carbon-carbon bond; and

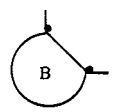

represents

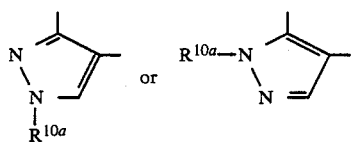

where $R^{10a}$ is hydrogen or $(C_1-C_3)$ alkyl, or a pharmaceutically acceptable salt thereof.

2. A compound of claim 1 wherein $R^4$ and $R^5$ combine to form a carbon-carbon bond.

3. A compound of claim 2 wherein $R^1$ is n-propyl.

4. A compound of claim 1 wherein $R^3$ is OH, $NH_2$, $NHCOR^9$ or $NHSO_2NR^9R^{10}$, where $R^9$ and $R^{10}$ are as defined in claim 1.

5. A compound of claim 4 wherein $R^1$ is n-propyl.

6. A compound of claim 4 as a racemate wherein the relative stereochemistry of the enantiomers is $(4a\beta,8\alpha,8a\alpha)$.

7. A compound of claim 4 as a racemate wherein the relative stereochemistry of the enantiomers is $(4a\beta,8\beta,8a\alpha)$.

8. A compound of claim 1 wherein $R^3$ and $R^5$ combine to form oxo or hydroxyamino and $R^2$ and $R^4$ are hydrogen.

9. A compound of claim 1 wherein $R^2$ is $CH_2OH$.

10. A compound of claim 1 wherein $R^2$ is $CH_2OCH_3$.

11. A compound of claim 1 wherein $R^2$ is $CH_2SCH_3$.

12. A compound of claim 1 wherein $R^2$ is $CO_2R^6$.

13. A compound of claim 1 wherein $R^3$ is OH.

14. A compound of claim 1 which is 7-(5-propyl-trans-4,4a,5,6,8a,9-hexahydro-2H(or 1H)-pyrazolo[3,4-g]quinoline)methanol, or a pharmaceutically acceptable salt thereof.

15. A pharmaceutical formulation comprising an effective amount of a compound of claim 1 associated with a pharmaceutically acceptable carrier or diluent therefor.

* * * * *

UNITED STATES PATENT AND TRADEMARK OFFICE
CERTIFICATE OF CORRECTION

PATENT NO. : 4,977,160

DATED : December 11, 1990

INVENTOR(S) : Diane L. Huser et al.

It is certified that error appears in the above-identified patent and that said Letters Patent is hereby corrected as shown below:

Claim 8, Column 58, line 8 - "hydroxyamino" should be -- hydroxyimino --.

Signed and Sealed this

Ninth Day of June, 1992

Attest:

DOUGLAS B. COMER

Attesting Officer

Acting Commissioner of Patents and Trademarks